United States Patent
Tanio et al.

(10) Patent No.: US 7,597,690 B2
(45) Date of Patent: Oct. 6, 2009

(54) SANITARY NAPKIN HAVING A PROTUBERANCE AND COMPRESSED PORTIONS

(75) Inventors: Toshiyuki Tanio, Kagawa (JP); Wataru Yoshimasa, Kagawa (JP); Kenichiro Kuroda, Kagawa (JP); Shinobu Fujikawa, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 419 days.

(21) Appl. No.: 11/123,608

(22) Filed: May 5, 2005

(65) Prior Publication Data

US 2005/0267433 A1    Dec. 1, 2005

(30) Foreign Application Priority Data

May 27, 2004    (JP) ............................. 2004-156963

(51) Int. Cl.
    *A61F 13/15* (2006.01)
(52) U.S. Cl. .................. 604/389; 604/390; 604/379; 604/385.01; 604/385.101; 604/385.27; 604/385.28
(58) Field of Classification Search ................ 604/389, 604/390, 379–380, 385.01, 385.101, 385.27, 604/385.28
    See application file for complete search history.

(56) References Cited

U.S. PATENT DOCUMENTS

| 2,896,618 | A | * | 7/1959 | Schaefer | 602/47 |
|---|---|---|---|---|---|
| 3,375,827 | A | * | 4/1968 | Bletzinger et al. | 604/380 |
| 4,758,240 | A | * | 7/1988 | Glassman | 604/379 |
| 4,770,657 | A | * | 9/1988 | Ellis et al. | 604/385.31 |
| 5,558,656 | A | * | 9/1996 | Bergman | 604/385.23 |
| 5,795,345 | A | * | 8/1998 | Mizutani et al. | 604/380 |
| 5,853,401 | A | * | 12/1998 | Mayer et al. | 604/378 |
| 6,042,575 | A | * | 3/2000 | Osborn et al. | 604/387 |
| 6,316,688 | B1 | * | 11/2001 | Hammons et al. | 604/378 |
| 6,371,948 | B1 | * | 4/2002 | Mizutani | 604/385.01 |
| 6,436,082 | B1 | * | 8/2002 | Mizutani et al. | 604/385.101 |
| 6,575,948 | B1 | * | 6/2003 | Kashiwagi et al. | 604/385.101 |
| 6,652,503 | B1 | * | 11/2003 | Bradley | 604/385.17 |
| 6,703,538 | B2 | * | 3/2004 | Lassen et al. | 604/378 |
| 7,132,585 | B2 | * | 11/2006 | Kudo et al. | 604/380 |
| 7,156,832 | B2 | * | 1/2007 | Drevik et al. | 604/385.31 |
| 2001/0021834 | A1 | * | 9/2001 | Yoshimasa | 604/385.01 |
| 2002/0068915 | A1 | * | 6/2002 | Drevik et al. | 604/385.01 |

FOREIGN PATENT DOCUMENTS

JP    11-042250    2/1999

(Continued)

OTHER PUBLICATIONS

Japanese International Search Report for PCT/JP2005/007637 mailed on Aug. 2, 2005.

*Primary Examiner*—Tatyana Zalukaeva
*Assistant Examiner*—Ginger T Chapman
(74) *Attorney, Agent, or Firm*—Darby & Darby P.C.

(57) ABSTRACT

A sanitary napkin includes a surface element that is formed of a liquid-permeable topsheet covering a liquid absorbent layer. The surface element is raised from the skin-side surface of a napkin body by an elastic force of an elastic member to form a protuberance having a front end and a rear end. The protuberance fits in the intergluteal cleft and prevents rearward leakage of menstrual blood.

8 Claims, 14 Drawing Sheets

FOREIGN PATENT DOCUMENTS

| | | |
|---|---|---|
| JP | 2000-083994 | 3/2000 |
| JP | 2001-504727 | 4/2001 |
| JP | 2002-320638 | 11/2002 |
| JP | 2004-528105 A | 9/2004 |
| WO | WO-02/087483 A1 | 11/2002 |

* cited by examiner

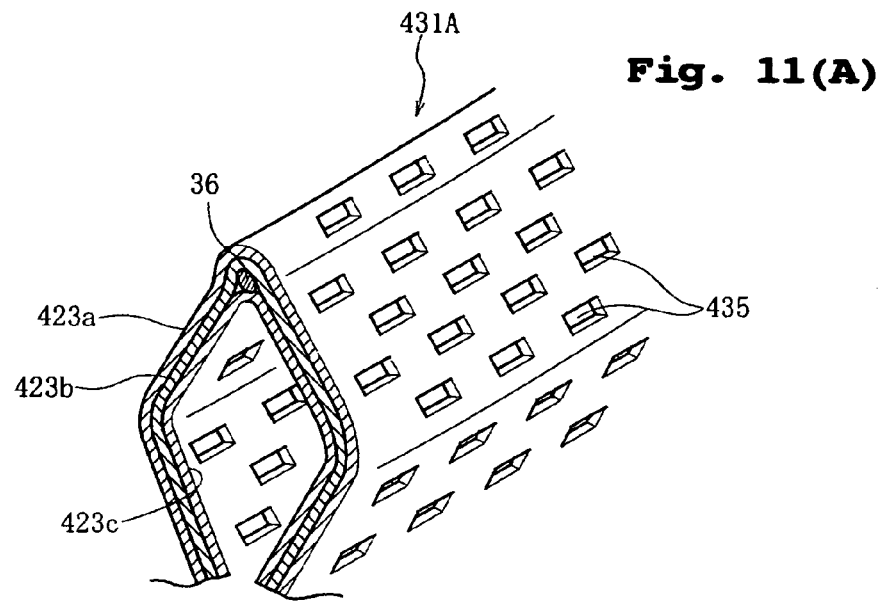
Fig. 11(A)
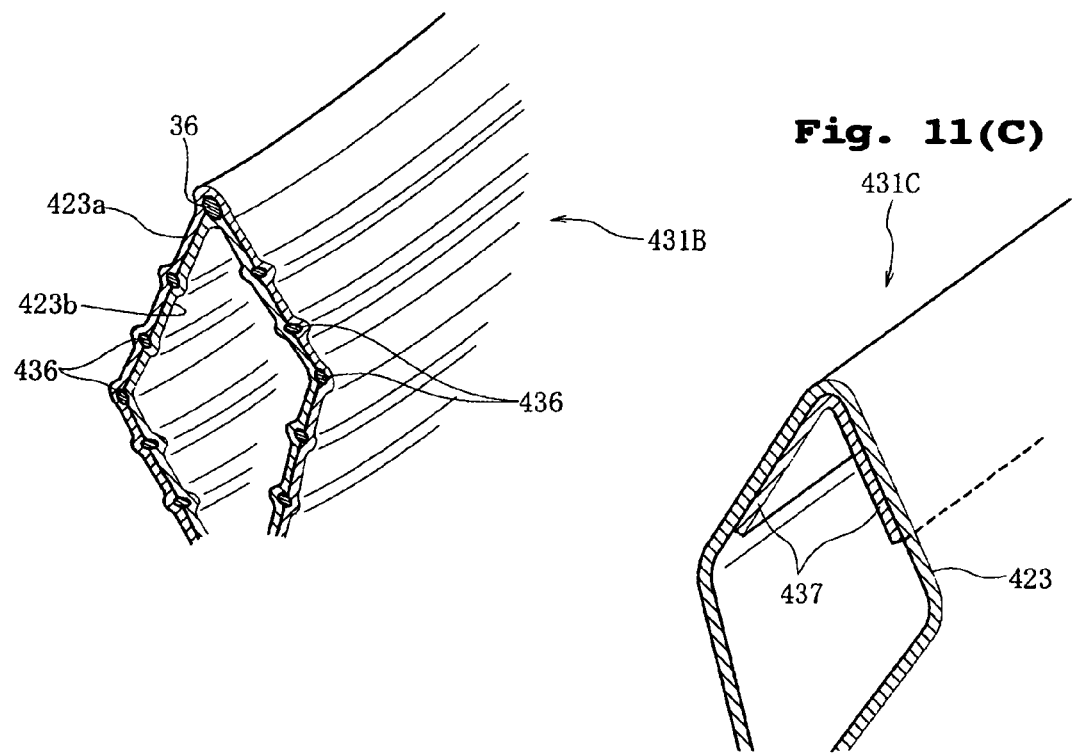
Fig. 11(B)
Fig. 11(C)

Fig. 14

SANITARY NAPKIN HAVING A PROTUBERANCE AND COMPRESSED PORTIONS

BACKGROUND OF THE INVENTION

1. Field of the Invention

The present invention relates to an elongated sanitary napkin having a vagina-facing region and an intergluteal cleft-facing region elongated rearward thereof and more particularly to a sanitary napkin which can be kept curved while being in close contact with the wearer's body from the posterior part of the vagina to the intergluteal cleft so as to be effective in preventing rearward leakage of menstrual blood during sleep.

2. Description of the Related Art

Conventional sanitary napkins include ones having a protruding structure, which is intended to come into close contact with the wearer's body, on a skin-side surface of a napkin body containing a liquid absorbent layer.

Patent Publication 1 identified below discloses a sanitary napkin in which a longitudinally extending elastic member is provided between a liquid absorbent layer and a topsheet covering the skin-side surface of the liquid absorbent layer. The elastic member extends between front and rear edges of the sanitary napkin and exhibits an elastic contractive force to bring the front and rear edges of the sanitary napkin closer to each other, so that the sanitary napkin is curved to have its skin-side surface recessed and also the center of the topsheet is lifted away from the liquid absorbent layer because of the elastic member. By keeping the topsheet thus lifted away from the liquid absorbent layer in close contact with the wearer's body, menstrual blood is allowed to be absorbed by the liquid absorbent layer via the topsheet.

Patent Publication 2 identified below discloses a sanitary napkin in which a three-dimensional structure, which is formed of a liquid-permeable sheet to have a T-shaped cross-section, is provided on the skin-side surface of a napkin body. The three-dimensional structure has a front end adjacent to a front edge of the napkin body and a rear end adjacent to a rear edge of the napkin body. The three-dimensional structure is provided with elastic members for exhibiting a longitudinal contractive force. These elastic members exert a force to bring the front and rear edges of the napkin body closer to each other so that the napkin body is curved, which makes the three-dimensional structure rise from the skin-side surface of the napkin body. This three-dimensional structure can be kept in close contact with the female genital organ and is aimed at providing a pleasant feeling during wear.

Patent Publication 3 identified below discloses a sanitary napkin in which an absorbent body and a stiffening element is disposed between a topsheet and a liquid absorbent layer and a hump of a triangular cross-section is formed of the topsheet, the absorbent body and the stiffening element. In the sanitary napkin disclosed in Patent Publication 3, the hump can conform to the groove between the labia majora without giving an unpleasant feeling to a wearer.

Patent Publication 4 identified below discloses a sanitary napkin having a heaped protrusion in a rear region of a skin-side surface. From the description of Patent Publication 4, it is unclear how the protrusion is constituted, but it describes that the protrusion comes into contact with the cleft of the buttocks to prevent rearward leakage of menstrual blood.

Patent Publication 1: Japanese Unexamined Patent Publication No. 2000-83994

Patent Publication 2: Japanese Unexamined Patent Publication No. 2002-320638

Patent Publication 3: Japanese Unexamined Patent Publication No. 2001-504727

Patent Publication 4: Japanese Unexamined Patent Publication No. H11-42250

In Patent Publications 1 and 2, the napkin body has a relatively short length and the sanitary napkin is designed to generally centrally face the vagina and is aimed chiefly at bring the liquid-permeable sheet, which is raised by the elastic member, into close contact with the vaginal opening. However, such a sanitary napkin having a relatively short length tends to be less effective in preventing rearward leakage of menstrual blood and therefore is not suitable for use while sleeping.

Suitable for use while sleeping is a sanitary napkin which is elongated to have a rear portion enabled to face the buttocks. In the sanitary napkins disclosed in Patent Publications 1 and 2, however, since an elastic contractive force of the elastic member acts between the front and rear edges of the napkin body, if the sanitary napkin is so elongated as to be suitable for use while sleeping, the elastic contractive force will act almost over the entire length of the elongated napkin body. Therefore, it becomes difficult for the napkin body to keep a sufficient stiffness to resist the elastic contractive force, and when the elastic member is pushed by the wearer's body to increase the elastic contractive force, the liquid absorbent layer may be wrinkled and contracted longitudinally or even folded to lower adhesion between the napkin body and the wearer's body, which results in impairing the effect of preventing leakage of menstrual blood toward the buttocks and also in causing lateral leakage of menstrual blood.

In the sanitary napkin disclosed in Patent Publication 3, on the other hand, the hump having a triangular cross-section easily comes into close contact with the vagina but is not able to easily enter the intergluteal cleft. This is because the body's groove is relatively wide and shallow in a region from the vaginal opening to the anus, but relatively narrow and deep in the anus and the intergluteal cleft where the opposing surfaces of the buttocks are brought closer to each other. Moreover, since the hump is formed of the absorbent body and the stiffening element, the portion having the hump cannot be easily curved to follow the contour of the buttocks. Therefore, making the napkin body longer tends to create a clearance between the napkin body and the wearer's body.

In the sanitary napkin disclosed in Patent Publication 4, the construction of the protrusion remains unclear, but this protrusion having a triangular cross-section over the entire length thereof cannot easily come into close contact with the narrow, deep intergluteal cleft where the opposing surfaces of the buttocks are brought closer to each other although it can fit the vaginal opening and the wide, shallow groove near the vaginal opening.

SUMMARY OF THE INVENTION

The present invention has been developed to solve the problems in the prior art set forth above and has an object to provide a sanitary napkin which can easily fit the intergluteal cleft and whose napkin body can be easily kept curved without being wrinkled or folded so as to effectively prevent rearward leakage of menstrual blood such as during sleep.

According to the present invention, there is provided an elongated sanitary napkin comprising: a napkin body containing a liquid absorbent layer for absorption and retention of liquid and having a vagina-facing region and an intergluteal cleft-facing region rearward of the vagina-facing region; and a protuberance located on a skin-side surface of the napkin body, the protuberance having a front end located in or rearward of the vagina-facing region and a rear end located in or rearward of the intergluteal cleft-facing region and being allowed to rise away from the skin-side surface of the napkin body to have an apex extending in a longitudinal direction of the napkin body between the front and rear ends, wherein the protuberance comprises a liquid-permeable sheet and an elastic member which exerts an elastic contractive force to bring the front and rear ends closer to each other for raising the liquid-permeable sheet away from the skin-side surface of the napkin body, wherein when no external force is exerted on the napkin body, a rising height of the protuberance from the skin-side surface of the napkin body is maximum at a position rearward of the vagina-facing region.

In the sanitary napkin according to the present invention, the protuberance formed of the liquid-permeable sheet and the elastic member for raising the liquid-permeable sheet can easily enter the intergluteal cleft so that menstrual blood flowing down the intergluteal cleft posteriorly such as during sleep can be prevented from leaking out from the napkin body. Moreover, since the elastic member exerts an elastic contractive force on the napkin body exclusively in a region behind the vagina-facing region, the napkin body is hardly wrinkled or folded by the elastic contractive force even though it is so elongated as to be suitable for use while sleeping.

Preferably, a stiffening element is provided in a rear portion of the napkin body to resist a bending force which acts to bring the front and rear ends closer to each other. With the stiffening element being provided in the napkin body, the rear portion of the napkin body can be easily kept curved to follow the contour of the buttocks.

Preferably, when the napkin body is mounted on a cylindrical surface having a radius of curvature of 110 mm such that a garment-side surface of the napkin body is in contact with the cylindrical surface with the longitudinal direction of the napkin body being oriented along a direction of curvature of the cylindrical surface and then the protuberance is pushed radially of the cylindrical surface at a position where the rising height is maximum by using a 30 mm diameter circular plane, a force required to depress the protuberance by 5 mm is in the range of 0.05 to 3 N while a force required to depress the protuberance to a level of 10 mm from the skin-side surface of the napkin body is in the range of 0.1 to 5 N. If the repulsive elastic force of the protuberance is in the above ranges, the protuberance can easily enter the intergluteal cleft and does not apply an excessive pressure to the wearer's body, which results in a comfortable feeling when worn.

Preferably, the elastic member is located on or adjacent to a longitudinal centerline of the napkin body so that the apex of the protuberance includes the elastic member.

Preferably, a front flattened portion where the liquid-permeable sheet is folded flat is provided forward of the front end with side edges located on both sides of and parallel to a longitudinal centerline of the napkin body. This front flattened portion is intended to come into close contact with the vaginal opening and the pubes. The front flattened portion is permeable to liquid and slightly bulges from the skin-side surface of the napkin body to come into close contact with the vaginal opening, thereby preventing formation of clearance between the vaginal opening and the napkin body.

Preferably, the protuberance is hollow. If the protuberance, most part of which is formed of the liquid-permeable sheet, is hollow, the protuberance can easily enter the narrow, deep intergluteal cleft.

For example, the liquid absorbent layer may be covered with the liquid-permeable sheet on both sides of the protuberance. Alternatively, the protuberance may be separated from the napkin body at a position between the front and rear ends so as to be freely movable. If the protuberance is freely movable at a position between the front and rear ends, the protuberance can be kept in the intergluteal cleft even when an undergarment is displaced with respect to the wearer's body such as by rolling over while sleeping.

The stiffening element may be compressed portions where the liquid absorbent layer is compressed. Preferably, the compressed portions comprise highly-compressed portions where the skin-side surface of the napkin body is recessed and weakly-compressed portions which have a lower density than the highly-compressed portions and alternate with the highly-compressed portions in the longitudinal direction of the napkin body. With the highly-compressed portions and the weakly-compressed portions thus alternating with each other, the rear portion of the napkin body can be easily curved to follow the contour of the buttocks and also prevented from being folded.

Alternatively, the stiffening element may be a reinforcing member incorporated into the napkin body.

According to the present invention, the protuberance easily comes into close contact with the intergluteal cleft. In addition, the napkin body can be easily curved to follow the contour of the wearer's body from the crotch to the buttocks and can also be easily kept in such a curved state. Therefore, the sanitary napkin in contact with the wearer's body is effective in preventing rearward leakage of menstrual blood.

BRIEF DESCRIPTION OF THE DRAWINGS

FIGS. 11(A), 11(B), 11(C) are partial perspective views showing protuberances according to different embodiments;

FIG. 14 is a sectional view showing a sanitary napkin according to a sixth embodiment of the present invention;

DESCRIPTION OF THE PREFERRED EMBODIMENT

Figure 1:
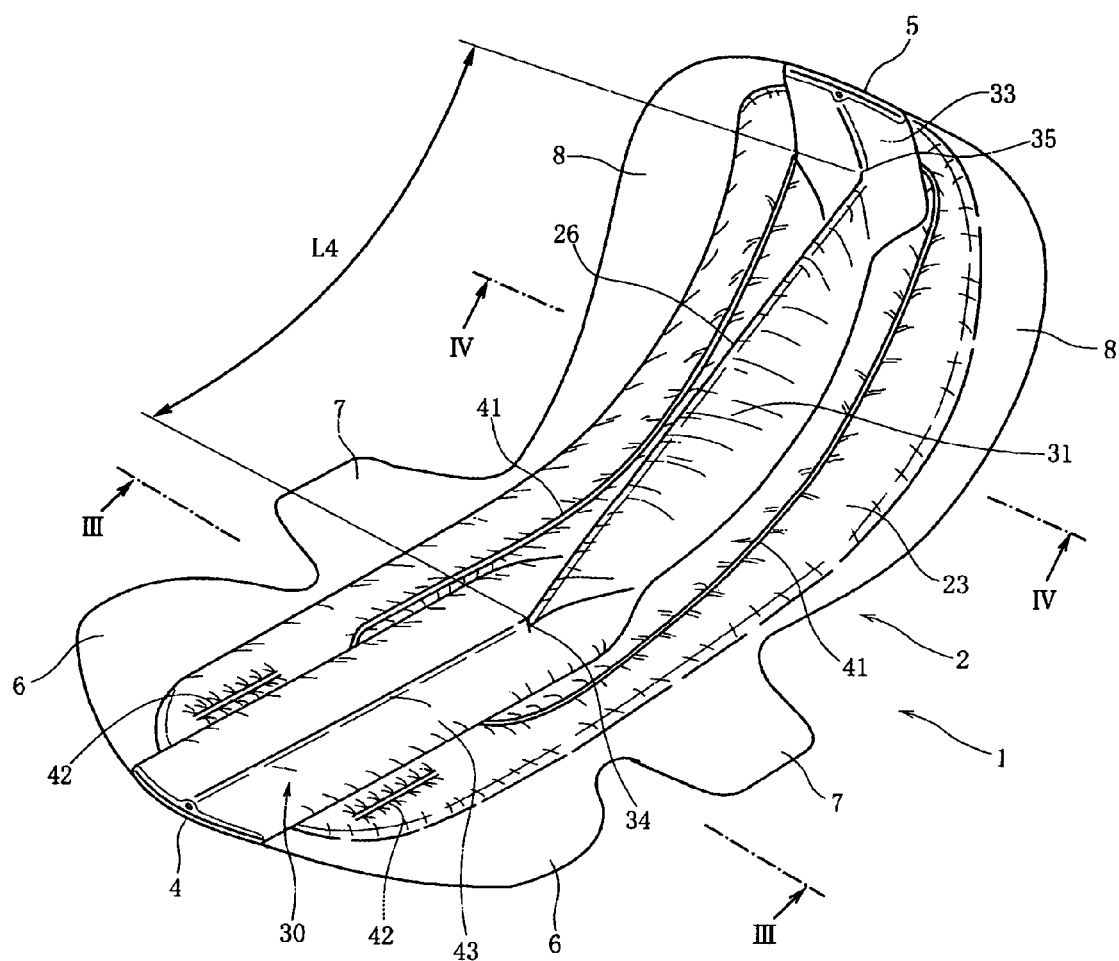
FIG. 1 is a perspective view showing a sanitary napkin according to a first embodiment of the invention in a free state where no external force is exerted.
Figure 2:
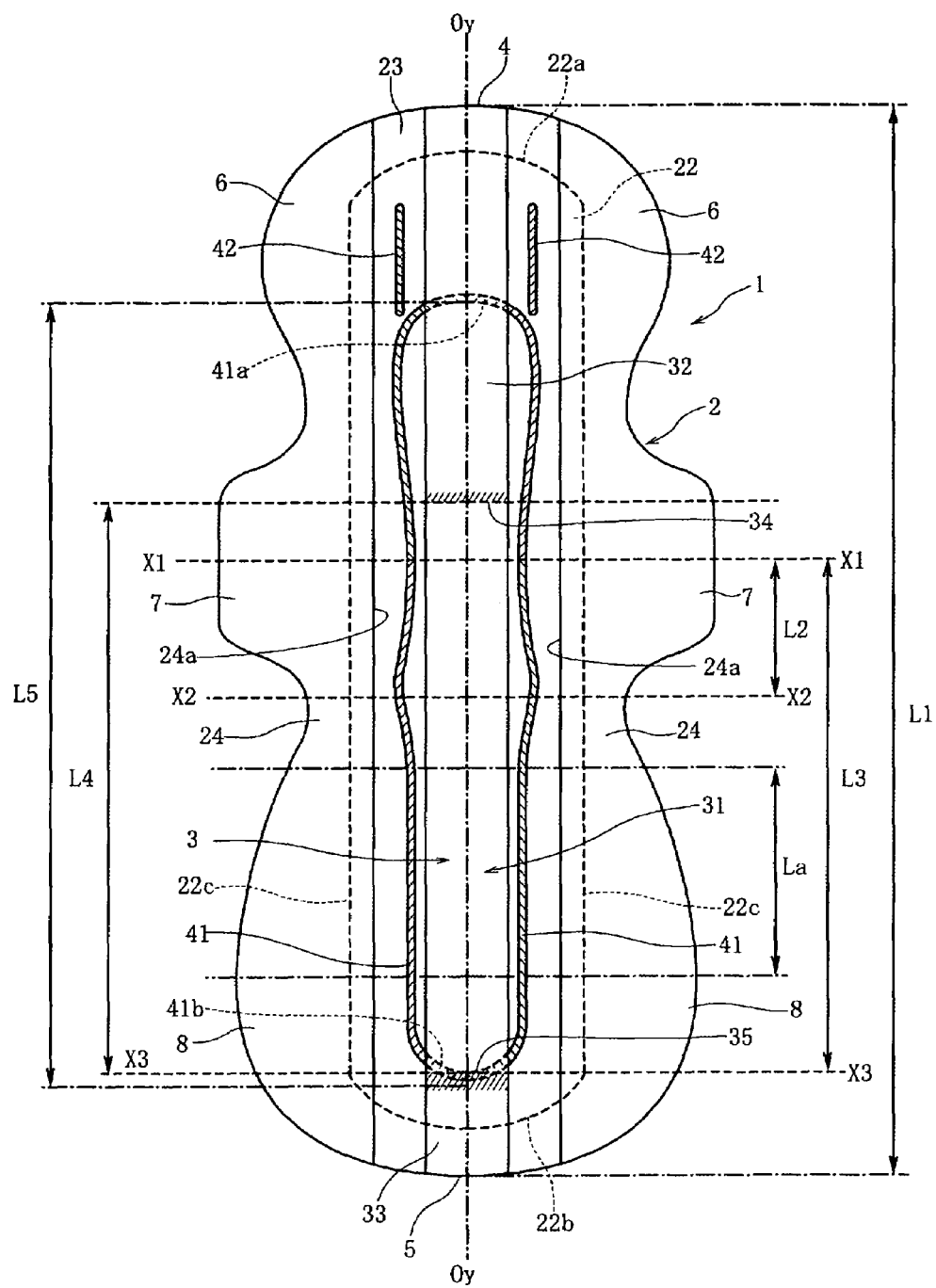
FIG. 2 is a plan view showing a state where the sanitary napkin is flattened on a plane.
Figure 3:
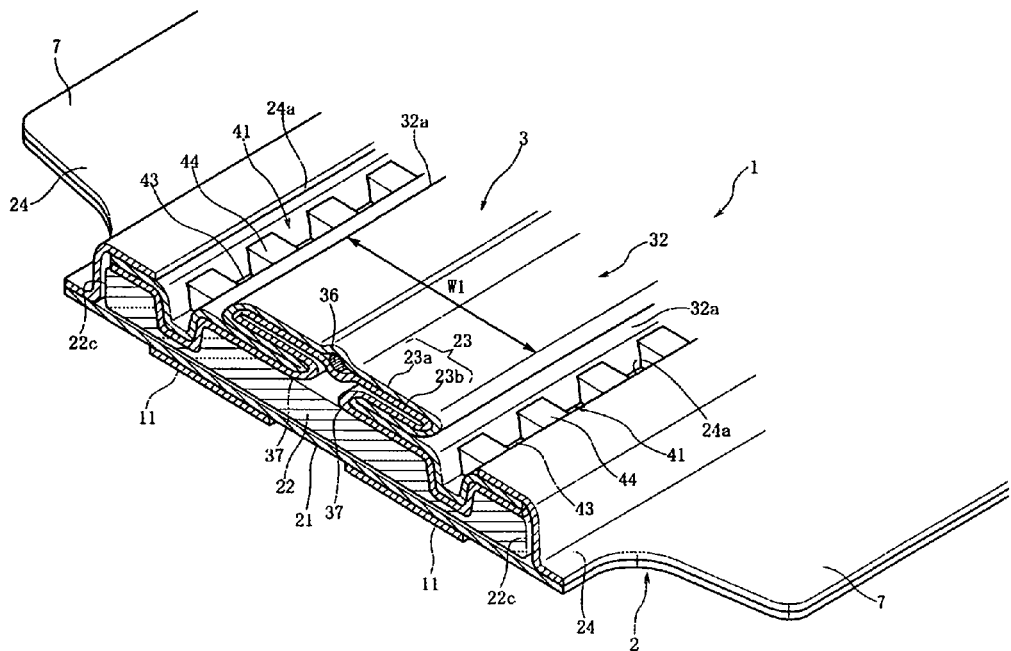
FIG. 3 is a sectional view taken along line III-III of FIG. 1.
Figure 4:
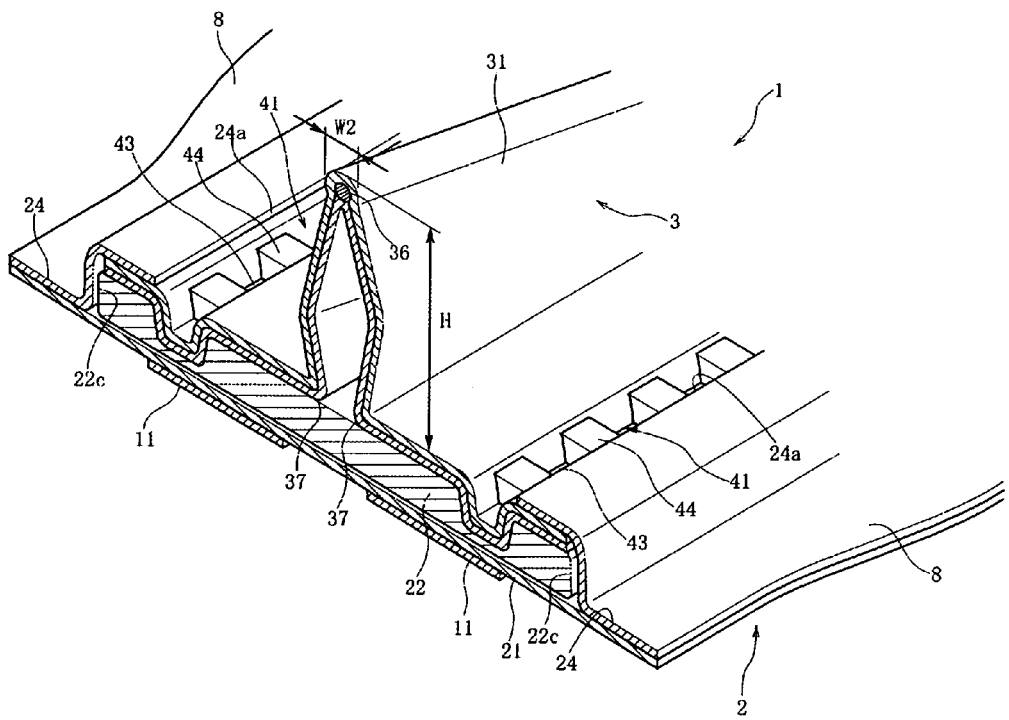
FIG. 4 is a sectional view taken along line IV-IV of FIG. 1.
Figure 5:
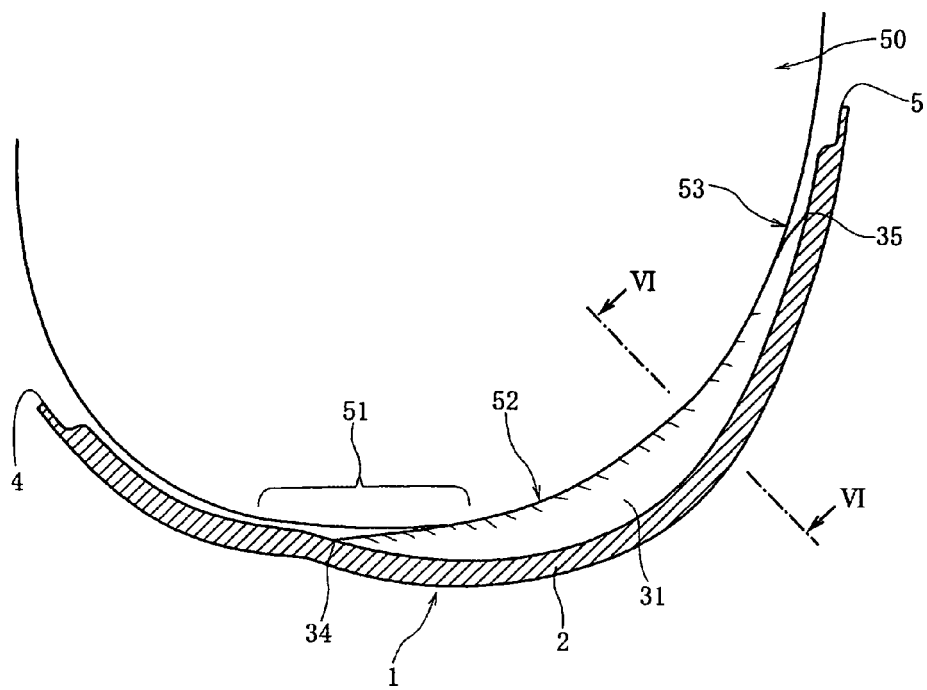
FIG. 5 is a longitudinal sectional view showing a state where the sanitary napkin is worn on the wearer's body.
Figure 6:
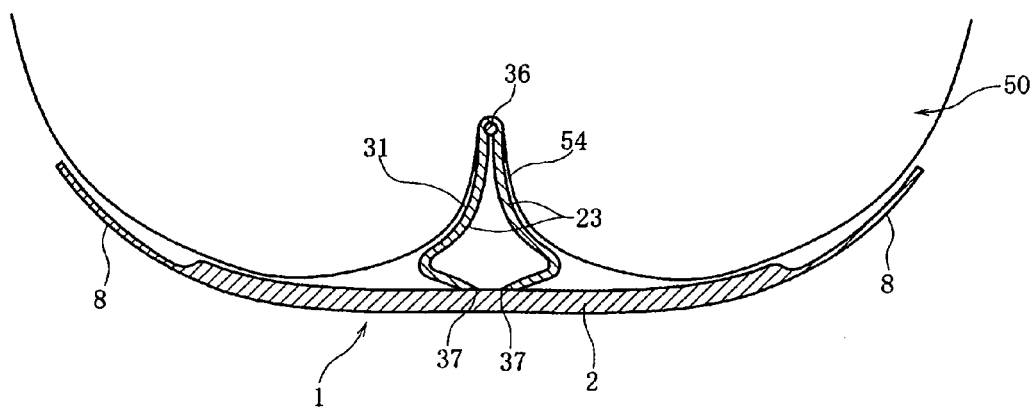
FIG. 6 is a sectional view taken along line VI-VI of FIG. 5.
Figure 7:
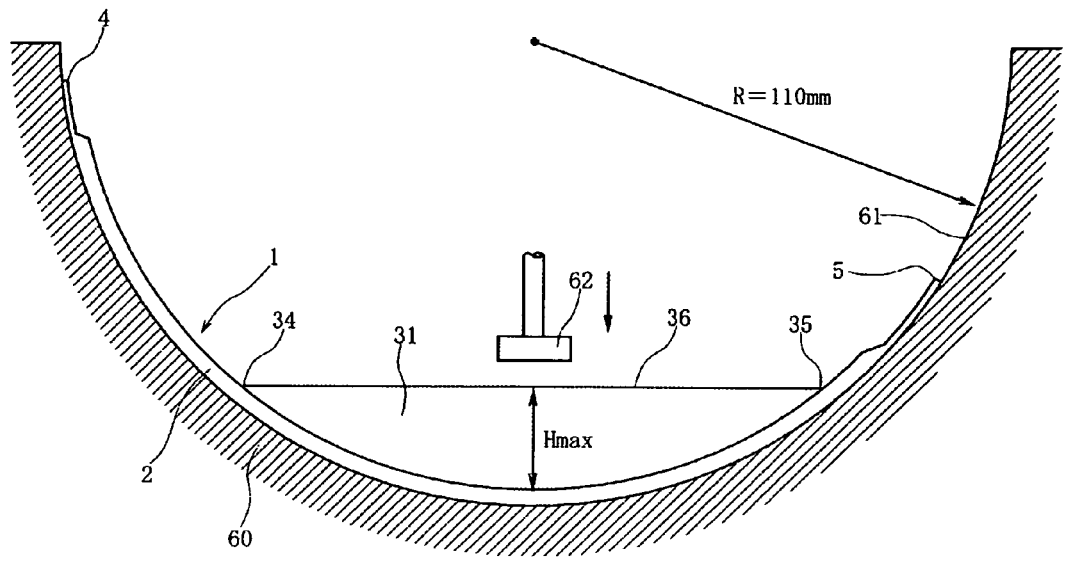
FIG. 7 is an explanatory drawing showing a method for measuring an elastic contractive force of an elastic member that is provided in a protuberance of the sanitary napkin.

FIG. 1 is a perspective view showing a sanitary napkin 1 according to a first embodiment of the invention in a free state where no external force is exerted. FIG. 2 is a plan view showing a state where the sanitary napkin 1 is flattened on a plane. FIG. 3 is a sectional view taken along line III-III of FIG. 1, and FIG. 4 is a sectional view taken along line IV-IV of FIG. 1. FIG. 5 is a sectional view schematically showing a state where the sanitary napkin 1 is applied to the wearer's body from the crotch to the buttocks, and FIG. 6 is a sectional view taken along line VI-VI of FIG. 5. FIG. 7 is a sectional view showing a method for measuring a repulsive elastic force of a protuberance of the sanitary napkin 1.

It should be noted that the sanitary napkin, as well as its individual components, has two major surfaces: of which one surface intended to be worn toward the wearer's crotch is referred to as "skin-side surface", while the other surface is referred to as "garment-side surface". In addition, the lengthwise direction of the sanitary napkin is referred to as "longitudinal direction", while the direction perpendicular to the longitudinal direction is referred to as "width direction". With respect to dimensions of the individual components, unless otherwise stated, a dimension measured in the longitudinal direction is referred to as "length", while a dimension measured in the width direction is referred to as "width".

The sanitary napkin 1 according to the first embodiment comprises a napkin body 2 and a surface element 3 located on the skin-side surface of the napkin body 2 for forming a protuberance.

As shown in FIGS. 3 and 4, the napkin body 2 comprises a liquid blocking backsheet 21 on its garment-side surface, a liquid absorbent layer 22 disposed on it, and a liquid-permeable topsheet 23 covering the liquid absorbent layer 22, wherein the surface element 3 is formed of a part of the topsheet 23.

As shown in FIG. 2, the napkin body 2 has a curved front end 4, as well as a curved rear end 5. The napkin body 2 is elongated to have a length L1 of 280 to 450 mm. The liquid absorbent layer 22 is also elongated, and the liquid absorbent layer 22 has a curved front end 22a spaced slightly inward from the front end 4 and a curved rear end 22b spaced slightly inward from the rear end 5. On the other hand, left and right side ends 22c, 22c of the liquid absorbent layer 22 extend linearly in parallel relationship with a longitudinal centerline Oy.

The napkin body 2 has front flaps 6, 6, fold-back flaps 7, 7 and rear flaps 8, 8 which project from the side ends 22c, 22c of the liquid absorbent layer 22. Here, the fold-back flaps 7, 7 are located rearward of the front flaps 6, 6 and the rear flaps 8, 8 are located rearward of the fold-back flaps 7, 7. In the front flaps 6, 6, fold-back flaps 7, 7 and rear flaps 8, 8, the backsheet 21 and liquid blocking side sheets 24 overlap with each other and are bonded to each other through a hot-melt type adhesive.

The side sheets 24, 24 disposed on opposite sides of the napkin body 2 in the width direction have opposing edges 24a, 24a inside the opposite side ends 22c, 22c of the liquid absorbent layer 22. At opposite sides of the liquid absorbent layer 22, as shown in FIGS. 3 and 4, the skin-side surface of the liquid absorbent layer 22 is covered with the topsheet 23 and the skin-side surface of the topsheet 23 is covered with the side sheets 24, 24. In a region defined between the opposing edges 24a, 24a of the side sheets 24, 24, the liquid-permeable topsheet 23 is exposed externally. The overlap between this region and a region where the liquid absorbent layer 22 is present is called liquid absorbent region.

X1 shown in FIG. 2 represents a vagina-facing reference line and this vagina-facing reference line X1 is spaced 100 to 200 mm rearwardly from the front end 4 of the napkin body 2, for example, spaced about 150 mm rearwardly from the front end 4.

The vagina-facing reference line X1 as used herein is a target position with which the center of the vaginal opening is to almost coincide when the sanitary napkin 1 is fixed to an undergarment and worn in the crotch. Leading to this target is through the contour of the sanitary napkin as viewed from the skin side or the whole design including the shape of compression lines on the skin-side surface, and particularly when the fold-back flaps 7, 7 are provided as in the present embodiment, the longitudinal centers of the fold-back flaps 7, 7 usually coincide with the target with which the center of the vaginal opening is to coincide.

In the present embodiment, accordingly, the line passing through the centers of the fold-back flaps 7, 7 is taken as the vagina-facing reference line X1.

X2 shown in FIG. 2 represents an anus-facing reference line and this anus-facing reference line X2 is intended to face the anus when the vagina-facing reference line X1 coincides with the center of the vaginal opening. The anus-facing reference line X2 is usually spaced a distance L2 of 30 to 70 mm, which varies depending on the wearer's body, rearwardly from the vagina-facing reference line X1.

X3 shown in FIG. 2 represents a coccyx-facing reference line. This coccyx-facing reference line X3 is intended to face the coccyx when the vagina-facing reference line X1 coincides with the center of the vaginal opening. The coccyx-facing reference line X3 is usually spaced a distance L3 of 120 to 180 mm, which varies depending on the wearer's body, rearwardly from the vagina-facing reference line X1. The rear end 5 of the napkin body 2 and the rear end 22b of the liquid absorbent layer 22 are located rearward of the coccyx-facing reference line X3.

In the napkin body 2, the area from a location 50 mm forward of the vagina-facing reference line X1 to the anus-facing reference line X2 is referred to as vagina-facing region, while the area from the anus-facing reference line X2 to the coccyx-facing reference line X3 is referred to as intergluteal cleft-facing region which is intended to face the intergluteal cleft. Throughout the disclosure, a hollow of the woman's body extending from a position anterior to the vaginal opening to the coccyx is referred to as body's groove, and of the body's groove, a groove extending from the anus to the coccyx is referred to as intergluteal cleft. The intergluteal cleft-facing region has a length in the range of 50 to 150 mm.

The backsheet 21 may be a film, for example, a polyethylene resin film having a basis weight of about 23 $g/m^2$, and is preferably permeable to moisture. The liquid absorbent layer 22 may be a mixture of fluff pulp and superabsorbent polymer (SAP) wrapped in a hydrophilic tissue, wherein the fluff pulp has a weight of about 400 $g/m^2$. The side sheet 24 may be a spunbonded nonwoven fabric of sheath/core bicomponent synthetic fibers, of which the core is polypropylene and the sheath is polyethylene.

The topsheet 23 is formed by laminating a first liquid-permeable sheet 23a and a second liquid-permeable sheet 23b. Both the first and second liquid-permeable sheets 23a, 23b are a through-air bonded nonwoven fabric having a basis weight of, for example, about 25 g/m². Constituent fibers of the through-air bonded nonwoven fabric may be sheath/core bicomponent synthetic fibers, of which the core is polyethylene terephthalate resin and the sheath is polyethylene resin and the core is mixed with an inorganic filler such as titanium oxide. The first and second liquid-permeable sheets 23a, 23b may be a mixture of 80% of hydrophilic fibers coated with a hydrophilic lubricant and 20% of water-repellent fibers coated with a water-repellent lubricant.

The first and second liquid-permeable sheets 23a, 23b are inseparably bonded to each other through a hot-melt type adhesive applied to such an extent as not to interfere with liquid passage (e.g., 2 g/m²).

The liquid-permeable sheet for the topsheet 23 may be a point-bonded nonwoven fabric, a spunlaced nonwoven fabric or a spunbonded nonwoven fabric, without limited to the through-air bonded nonwoven fabric, but its fiber density is preferably equal to or less than 0.12 g/cm³ so as to improve liquid permeability. In an alternative, the liquid-permeable sheet may be a resin film formed with a large number of liquid passage apertures, for example, the first liquid-permeable sheet 23a may be such a resin film formed with liquid passage apertures while the second liquid-permeable sheet 23b may be a nonwoven fabric such as through-air. Here, the topsheet 23 may be embossed with a dot pattern or corrugated.

The surface element 3 disposed on the skin-side surface of the napkin body 2 is constructed of the topsheet 23. More specifically, a part of the topsheet 23 forms the surface element 3 and the rest of the topsheet 23 (i.e., the part not forming the surface element 3) is bonded to the skin-side surface of the liquid absorbent layer 22 through a hot-melt type adhesive applied to such an extent as not to interfere with liquid passage.

As shown in FIG. 2, the surface element 3 has a protuberance 31 with front and rear ends 34, 35, a front flattened portion 32 between the front end 34 and the front end 4 of the napkin body 2, and a rear flattened portion 33 between the rear end 35 and the rear end 5 of the napkin body 2.

An elastic member 36 is disposed at least in the protuberance 31 of the surface element 3 to extend longitudinally. According to the present embodiment, the elastic member 36 is disposed to extend from a position forward of the front end 34 to a position rearward of the rear end 35.

As shown in FIGS. 3 and 4, the elastic member 36 is disposed on the longitudinal centerline Oy and interposed between the first and second liquid-permeable sheets 23a, 23b. The elastic member 36 is bonded to both the first and second liquid-permeable sheets 23a, 23b through a hot-melt type adhesive.

The elastic member 36 is a polyurethane elastic string having a fineness in the range of 420 to 10000 dtex, preferably in the range of 1800 to 8000 dtex. In an alternative, the elastic member 36 may be a rubber thread made of a natural or synthetic rubber. The elastic member 36 is fixed between the first and second liquid-permeable sheets 23a, 23b while being stretched to at least 1.2 times, preferably 1.5 times its original length between the front and rear ends 34, 35.

Between the front and rear ends 34, 35, the elastic member 36 is allowed to move away from the skin-side surface of the napkin body 2 between the front and rear ends 34, 35. When no external force is exerted on the sanitary napkin, therefore, the elastic member 36 exerts an elastic contractive force to bring the front and rear ends 34, 35 closer to each other, as shown in FIG. 1.

As shown in FIGS. 3 and 4, join boundary lines 37, 37 extend in parallel to the longitudinal direction at equal distances from the longitudinal centerline Oy. Outside the join boundary lines 37, 37, the topsheet 23 is bonded to the skin-side surface of the liquid absorbent layer 22. In the front flattened portion 32, the topsheet 23 between the join boundary lines 37, 37 is folded flat as shown in FIG. 3 and the overlaps are bonded together through a hot-melt type adhesive so as not to move away from the skin-side surface of the napkin body 2.

In the front flattened portion 32, moreover, the part of the topsheet 23 having the elastic member 36 is bonded to the liquid absorbent layer 22 so that the elastic member 36 does not rise away from the skin-side surface of the napkin body 2.

The front flattened portion 32 has side edges 32a, 32a at equal distances from the longitudinal centerline Oy and has a width W1 in the range of 10 to 50 mm. When the sanitary napkin 1 is put on, the front flattened portion 32 comes into contact with the anterior part of the vaginal opening. If the width W1 of the front flattened portion 32 is in the above range, the front flattened portion 32 can be easily kept in close contact with the vaginal opening to ensure that menstrual blood discharged from the vaginal opening passes through the front flattened portion 32 in close contact with the vaginal opening and is led to the underlying liquid absorbent layer 22. It should be noted that the rear flattened portion 33 has the same construction as the front flattened portion 32.

The elastic member 36 exerts an elastic contractive force to bring the front and rear ends 34, 35 closer to each other, so that the napkin body 2 is curved with the skin-side surface recessed as shown in FIG. 1. As a result, the elastic member 36 between the front and rear ends 34, 35 is moved away from the skin-side surface of the napkin body 2 to raise the topsheet 23 into a three-dimensional shape with the lower end at the join boundary lines 37, 37, as shown in FIG. 4.

As shown in FIG. 2, the front end 34 is located forward of the vagina-facing reference line X1 of the napkin body 2 and within the vagina-facing region. However, the location of the front end 34 is not limited to this point, because the location and size of the vaginal opening vary between individuals and the location where the vagina opening faces within the vagina-facing region may also vary depending on how the sanitary napkin 1 is worn. Accordingly, the front end 34 may be located within 50 mm forward and rearward from the vagina-facing reference line X1 and spaced at least 50 mm rearward from the front end 4 of the napkin body 2. The rear end 35 may be located slightly forward or rearward of the coccyx-facing reference line X3.

Here, it is required that most part of the protuberance 31 is present in the intergluteal cleft-facing region (i.e., the region between the anus-facing reference line X2 and the coccyx-facing reference line X3). As long as this requirement is satisfied, the front end 34 may be spaced rearward from the vagina-facing region. Preferably, the protuberance 31 has a length L4 in the range of 50 to 300 mm.

As shown in FIGS. 1 and 2, the skin-side surface of the napkin body 2 is formed with compressed portions where the topsheet 23 and the liquid absorbent layer 22 are compressed and heated together. The compressed portions form a main compressed line 41 which extends continuously from a position forward of the front end 34 to a position rearward of the rear end 35. The compressed portions also form front compressed lines 42 forward of the main compressed line 41.

The main compressed line 41 is formed within a region having a length L5 which is longer than the length L4 of the protuberance 31, and the main compressed line 41 extends longitudinally along the protuberance 31. The main compressed line 41 is symmetrical about the longitudinal centerline Oy. In the present embodiment, the main compressed line 41 is curved to bulge near the anus-facing reference line X2, but it may take various shapes. For example, the main compressed line 41 may be parallel to the longitudinal centerline Oy all along the protuberance 31.

As shown in FIG. 2, the main compressed line 41 has a front portion 41a and a rear portion 41b to enclose an elongated region where the liquid absorbent layer 22 is present. However, the front portion 41a and/or the rear portion 41b may be omitted.

The main compressed line 41 functions as a stiffening element which provides the napkin body 2 with a proper stiffness to resist an elastic contractive force of the elastic member 36.

As shown in FIGS. 3, 4, 12(A) and 12(B), the main compressed line 41 is formed by longitudinally alternating highly-compressed portions 43 with weakly-compressed portions 44, and the skin-side surface of the napkin body 2 is deeply recessed in the individual highly-compressed portions 43. The highly-compressed portions 43 are at least twice, preferably at least 5 times as high as uncompressed portion of the liquid absorbent region in density of the liquid absorbent layer 22. On the other hand, the weakly-compressed portions 44 have a lower density than the highly-compressed portions 43 but are at least 1.5 times, preferably at least twice as high as the uncompressed portion of the liquid absorbent region in density of the liquid absorbent layer 22.

Although the napkin body 2 is subjected to an elastic contractive force of the elastic member 36 to bring the front and rear ends 34, 35 closer to each other, the main compressed line 41 prevents the liquid absorbent layer 22 from being wrinkled and contracted longitudinally or folded between the front and rear ends 34, 35.

When no external force is exerted on the napkin body 2, therefore, the napkin body 2 can be kept in such a curved state as shown in FIG. 1 with an appropriate curvature between the front and rear ends 34, 35.

Figure 12A:
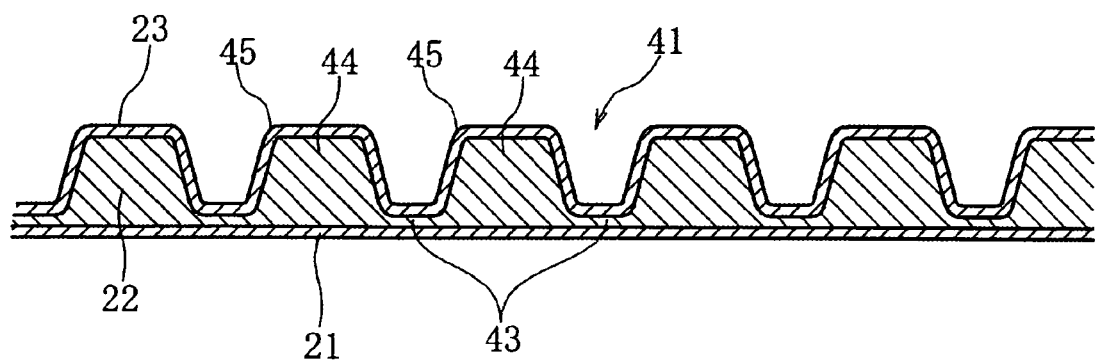
FIG. 12(A) is a sectional view of a compressed line.
Figure 12B:
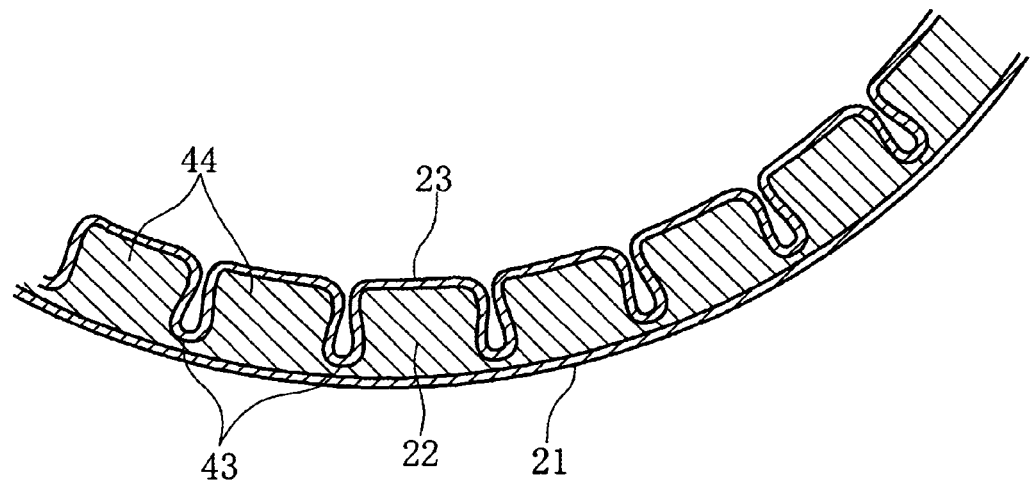
FIG. 12(B) is a sectional view showing the compressed line in a curved state.

More specifically, because the main compressed line 41 is formed by longitudinally alternating the highly-compressed portions 43 and the weakly-compressed portions 44 and the skin-side surface of the napkin body 2 is deeply recessed at the highly-compressed portions 43, as shown in FIG. 12(A), when an elastic contractive force acts between the front and rear ends 34, 35, the liquid absorbent layer 22 can be easily deformed to bring tops of the weakly-compressed portions 44 into close contact with each other, as shown in FIG. 12(B). Therefore, when the elastic member 36 exerts an elastic contractive force, the rear portion of the napkin body 2 can be easily curved as shown in FIG. 1, while the napkin body 2 can be prevented from being folded because the weakly-compressed portions 44 come into close contact with each other.

Here, because the sanitary napkin 1 is sufficiently long to have the vaginal-facing region and the intergluteal cleft-facing region, it will be typically folded for packaging. When packaging, the sanitary napkin 1 may be folded on a fold line crossing the protuberance 31. However, since the main compressed line 41 is provided as the stiffening element along the protuberance 31, the napkin body 2 can be prevented from being forcibly folded by the elastic member 36 at positions other than the fold line that is formed at the time of packaging.

Accordingly, if a fold line for packaging is located midway between the front and rear ends 34, 35, undesirable folding at positions other than the fold line and formation of an undesirable bulge at a position forward of the fold line can be prevented, so that the napkin body 2 can be kept in such a curved state as shown in FIG. 1.

When no external force is exerted on the napkin body 2, a rising height H of the protuberance 31 from the skin-side surface of the napkin body 2 is maximum at the midpoint between the front and rear ends 34, 35. The location where the rising height H is maximum is spaced about 10 to 50 mm rearward from the anus-facing reference line X2.

The maximum rising height H is preferably in the range of 10 to 60 mm. If it is below the range, the protuberance 31 cannot reach the deepest part of the intergluteal cleft; if it is above the range, the elastic member 36 provided in the protuberance 31 will exert an excessive pressure on the intergluteal cleft to give an unpleasant feeling to the wearer's body from the anus to the coccyx.

On the other hand, the protuberance 31 rising as shown in FIG. 4 preferably has an apex width W2 in the range of 1 to 3 mm. If it is within the range, the apex of the protuberance 31 can easily enter the intergluteal cleft to collect menstrual blood trying to migrate posteriorly along the intergluteal cleft.

As shown in FIGS. 3 and 4, pressure-sensitive adhesive layers 11 are disposed on the garment-side surface of the backsheet 21 so as to fix the napkin body 2 on an undergarment. The pressure-sensitive adhesive layers 11 are located on both sides of and parallel to the longitudinal centerline Oy. The pressure-sensitive adhesive layers 11 are in the shape of strips extending over the entire length of the napkin body 2. Preferably, the pressure-sensitive adhesive layers 11 are disposed all along the protuberance 31; more preferably, the pressure-sensitive adhesive layers 11 are located beneath the main compressed line (stiffening element) 41, as shown in FIG. 4.

With the napkin body 2 being fixed on an undergarment along the main compressed line 41, the stiffening element is further reinforced to prevent the napkin body 2 from being wrinkled or folded during wear within the region having the protuberance 31.

Although omitted in the drawings, it should be noted that the fold-back flaps 7, 7 and the rear flaps 8, 8 also have pressure-sensitive adhesive layers on the garment-side surface of the backsheet 21.

When using the sanitary napkin 1, the pressure-sensitive adhesive layers 11, 11 on the garment-side surface of the napkin body 2 are adhered to the inner side of the undergarment. Then, the fold-back flaps 7, 7 are folded back upon the outer side of the undergarment along two side edges of a crotch part of the undergarment and then the pressure-sensitive adhesive layers on the garment-side surfaces of the fold-back flaps 7, 7 are adhered to the outer side of the crotch part. In addition, the pressure-sensitive adhesive layers on the garment-side surfaces of the rear flaps 8, 8 are adhered to the inner side of the undergarment at a lower part of a back body.

When the sanitary napkin 1 is adhered to the undergarment by a user, the center location between the fold-back flaps 7, 7 (the vagina-facing reference line X1) serves as a target for positioning so that it is worn with the center location almost coinciding with the longitudinal center of the vaginal opening.

FIGS. 5(A) and 5(B) show a state where the sanitary napkin 1 is worn from the crotch to the buttocks of a woman's body 50. In FIG. 5(A), the location of the vaginal opening is indicated by the numeral 51, the location of the anus is indicated by the numeral 52, and the location of the coccyx is indicated by the numeral 53. The woman's body has a groove from an anterior part of the vaginal opening to the coccyx, of which the intergluteal cleft extends from the location of the anus 52 to the location of the coccyx 53. On the other hand, the crotch is located anterior to the location of the anus 52.

Since the elastic contractive force of the elastic member 36 does not act on a front portion of the napkin body 2, the front portion can be deformed to flexibly fit the vaginal opening and the mons pubis anterior to the vaginal opening. On the other hand, since the elastic contractive force of the elastic member 36 intensively acts on the rear portion of the napkin body 2, the napkin body 2 behind the vagina-facing region can be curved to closely fit the buttocks.

Here, since the protuberance is mainly formed of the topsheet 23 (the first and second liquid-permeable sheets 23a, 23b), its cross-sectional shape is allowed to change freely in accordance with the shape of the crotch and the shape of the intergluteal cleft.

In the sanitary napkin 1, since the location where the rising height of the protuberance 31 is maximum is behind the anus-facing reference line X2, the protuberance 31 is relatively low and wide in the portion intended to contact the crotch anterior to the location of the anus 52. In the crotch, accordingly, the protuberance 31 can closely fit the wearer's body while being crushed down.

As shown in FIG. 6, the intergluteal cleft is narrow and deep and indicated by the numeral 54. Since the protuberance 31 is relatively high in the portion intended to enter the intergluteal cleft 54, the protuberance 31 is gradually narrowed toward the apex. Thus, the protuberance 31 can reach the deepest part of the intergluteal cleft 54.

Since the protuberance 31 is hollow, the protuberance 31 is allowed to be deformed in accordance with the shape from the crotch to the intergluteal cleft 54, as set forth above. Here, as far as the protuberance 31 is flexibly deformable in accordance with the shape from the crotch to the intergluteal cleft 54, a thin absorbent sheet such as of pulp may be provided on an inner surface of the topsheet 23, without limited to the one which is mainly formed of the topsheet 23.

Since the first and second liquid-permeable sheets 23a, 23b forming the front flattened portion 32 comes into close contact with the anterior part of the vaginal opening, menstrual blood discharged from the vaginal opening passes through spaces between fibers of the liquid-permeable sheets 23a, 23b under gravitation in the front flattened portion 32 and is quickly absorbed and retained by hydrophilic power of the underlying liquid absorbent layer 22. On the other hand, menstrual blood trying to flow down the intergluteal cleft 54 posteriorly from the vaginal opening such as during sleep is collected by the protuberance 31 in close contact with the intergluteal cleft 54.

Menstrual blood given to the protuberance 31 reaches the skin-side surface of the napkin body 2 through the liquid-permeable sheets 23a, 23b forming this protuberance 31 and is quickly absorbed and retained by the liquid absorbent layer 22. Therefore, menstrual blood is less apt to leak out from the sanitary napkin 1 toward the buttocks.

When the sanitary napkin 1 is put on, the elastic member 36 exerts a pressure on the body 50, but this pressure does not act on the vaginal opening very much but chiefly acts on the intergluteal cleft 54 posterior to the vaginal opening, so that it can be worn comfortably.

Preferred values of properties of the sanitary napkin 1 will be described hereinbelow.

When the sanitary napkin 1 is forcibly developed to flatten its garment-side surface, as shown in FIG. 2, a force required to bring the front and rear ends 34, 35 closer to each other is preferably between 0.1 and 5.0 N. If it is below the range, the force of the elastic member 36 will be too weak to deform the rear portion of the napkin body 2 into such a curved shape as shown in FIG. 1. If it is above the range, on the other hand, the elastic member 36 will be disengaged between the front and rear ends 34, 35 in such a flattened state as shown in FIG. 2.

The elastic contractive force of the elastic member 36 and the stiffness of the napkin body 2 are set such that when the sanitary napkin 1 is allowed to be curved with the elastic contractive force acting between the front and rear ends 34, 35, the napkin body 2 is maintained in such a curved shape as shown in FIG. 1, wherein the elastic contractive force will not result in folding of the napkin body 2 and the liquid absorbent layer 22 will not contract in the longitudinal direction.

In order to maintain the napkin body 2 in such a curved shape, the elastic contractive force of the elastic member 36 and the stiffness of the napkin body 2 are preferably as follows.

FIG. 7 is an explanatory drawing showing a method for measuring an elastic contractive force of the elastic member 36. A measurement jig 60 has a concave cylindrical surface 61 with a radius R=110 mm. The radius R=110 mm corresponds approximately to an average curvature of a curve from the crotch to the buttocks taken along a median plane of an adult woman who is 27 years old, stands 168 cm tall, weights 56 kg and has a BMI of 19.8. As a measuring device, used is a pusher 62 which is allowed to move straight radially of the cylindrical surface 61. The pusher 62 has a contact surface (i.e., surface to be brought into contact with an object) which is flat and circular with a diameter of 30 mm.

The garment-side surface of the sanitary napkin 1 is fixed on the cylindrical surface 61 through the pressure-sensitive adhesive layers 11 with the longitudinal direction of the sanitary napkin 1 being oriented along the direction of curvature of the cylindrical surface 61. At the location where the apex has a maximum rising height $H_{max}$ from the skin-side surface of the napkin body 2, then, the protuberance 31 is pushed by the pusher 62 at a rate of 20 mm/min linearly and radially of the cylindrical surface 61.

At this time, a force required to depress the apex of the protuberance 31 by 5 mm is preferably in the range of 0.05 to 3 N, more preferably in the range of 0.05 to 1 N per 10 mm length of the protuberance 31. On the other hand, a force required to depress the protuberance 31 to a level of 10 mm from the skin-side surface of the napkin body 2 is preferably in the range of 0.1 to 5 N, more preferably in the range of 0.3 to 2.0 N per 10 mm length of the protuberance 31.

Within the above ranges, the protuberance 31 can easily enter the intergluteal cleft 54 and a pressure on the intergluteal cleft 54 will be less bothersome during wear.

For measurement of the stiffness of the napkin body 2, the elastic member 36 is removed from the sanitary napkin 1 of FIG. 2 and then a sample having a size of 50×50 mm is cut out from the sanitary napkin 1 at a position midway between the anus-facing reference line X2 and the coccyx-facing reference line X3 with center at the longitudinal centerline Oy to include opposing parts of the main compressed line 41 on both sides thereof. The opposite ends of the sample in the longitudinal direction of the sanitary napkin 1 are held by chucks with a chuck distance of 40 mm. The maximum load acting between the chucks is measured as the chucks are brought closer to each other at a rate of 10 mm/min until the chuck distance becomes 20 mm.

According to this measurement, the maximum load (buckling load) is preferably in the range of 0.5 to 6 N, more preferably in the range of 1 to 3 N.

After the elastic member 36 is removed, another sample having a length La=150 mm is cut out from the sanitary napkin 1 of FIG. 2 at a position midway between the anus-facing reference line X2 and the coccyx-facing reference line X3.

The longitudinal opposite ends of the sample are held by chucks using an automatic bending tester (KES-FB2-L) manufactured by KATO TECH CO., LTD. Then, the sample is bent in opposite directions within the curvature range of 0.5 cm$^{-1}$ on the plus side and 0.5 cm$^{-1}$ on the minus side at a curvature change rate of 0.1 cm$^{-1}$ min to obtain a hysteresis curve of bending moment required to bend the sample in either direction. When the curvature is 0.1 cm$^{-1}$, hysteresis of bending moment is 2 HB. 2 HB is preferably equal to or greater than $3 \times 10^{-2}$ (N·m/m) and equal to or less than $15 \times 10^{-2}$ (N·m/m), more preferably equal to or less than $10 \times 10^{-2}$ (N·m/m).

If the elastic force of the elastic member 36 and the stiffness of the napkin body 2 are set within the above ranges, the rear portion of the napkin body 2 can be kept curved in both the state where no external force is exerted and the state where the garment-side surface is curved with a radius R=110 mm (i.e., where the sanitary napkin 1 is worn), effectively preventing the napkin body 2 from being contracted longitudinally or folded.

It should be noted that the sanitary napkin 1 may be used in combination with a tampon or an interlabia pad to be worn between the labia of the vagina. Since the protuberance 31 extends from adjacent the vaginal opening and along the intergluteal cleft, the tampon or interlabia pad used in combination with the sanitary napkin 1 can be prevented from being displaced or disengaged.

Hereinbelow, sanitary napkins according to other embodiments of the present invention will be described. In the following embodiments, the detailed description of the portions having the same construction as those of the first embodiment will be omitted by designating them by the common reference numerals.

Figure 8:
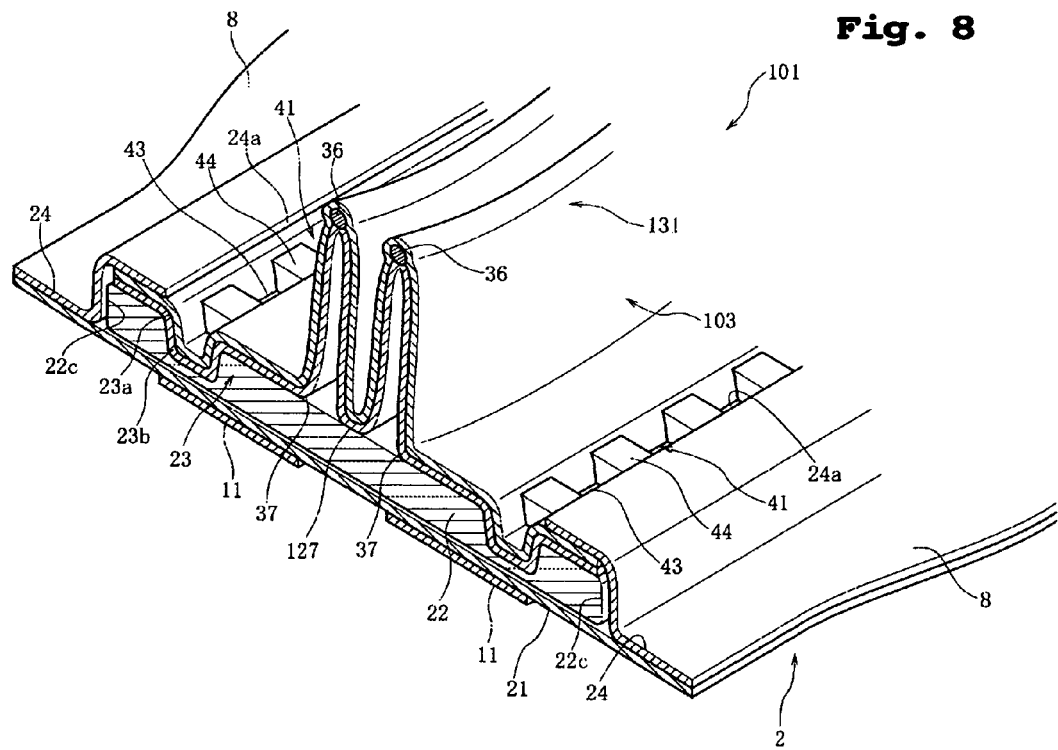
FIG. 8 is a sectional view showing a sanitary napkin according to a second embodiment of the present invention.

FIG. 8 shows a sanitary napkin 101 according to a second embodiment of the present invention and is a sectional view corresponding to FIG. 4.

The sanitary napkin 101 according to the second embodiment has a surface element 103 on the napkin body 2. In the surface element 103, two elastic members 36, 36 are adhesion-bonded between the first and second liquid-permeable sheets 23a, 23b. At a location 127 midway between the locations where the individual elastic members 36, 36 are bonded, the topsheet 23 is bonded to the skin-side surface of the liquid absorbent layer 22. As shown in FIG. 8, the location 127 is at equal distances from the join boundary lines 37, 37.

The elastic members 36, 36 are located on both sides of and parallel to the longitudinal centerline Oy. Thus, the surface element 103 provides a protuberance 131 having two longitudinally extending apexes. The apexes disposed close to each other can easily enter the intergluteal cleft 54. Moreover, menstrual blood trying to move rearward on the surface of the sanitary napkin 101 can be introduced into the groove between the two apexes, enhancing the effect of preventing rearward leakage of menstrual blood such as during sleep.

Figure 9:
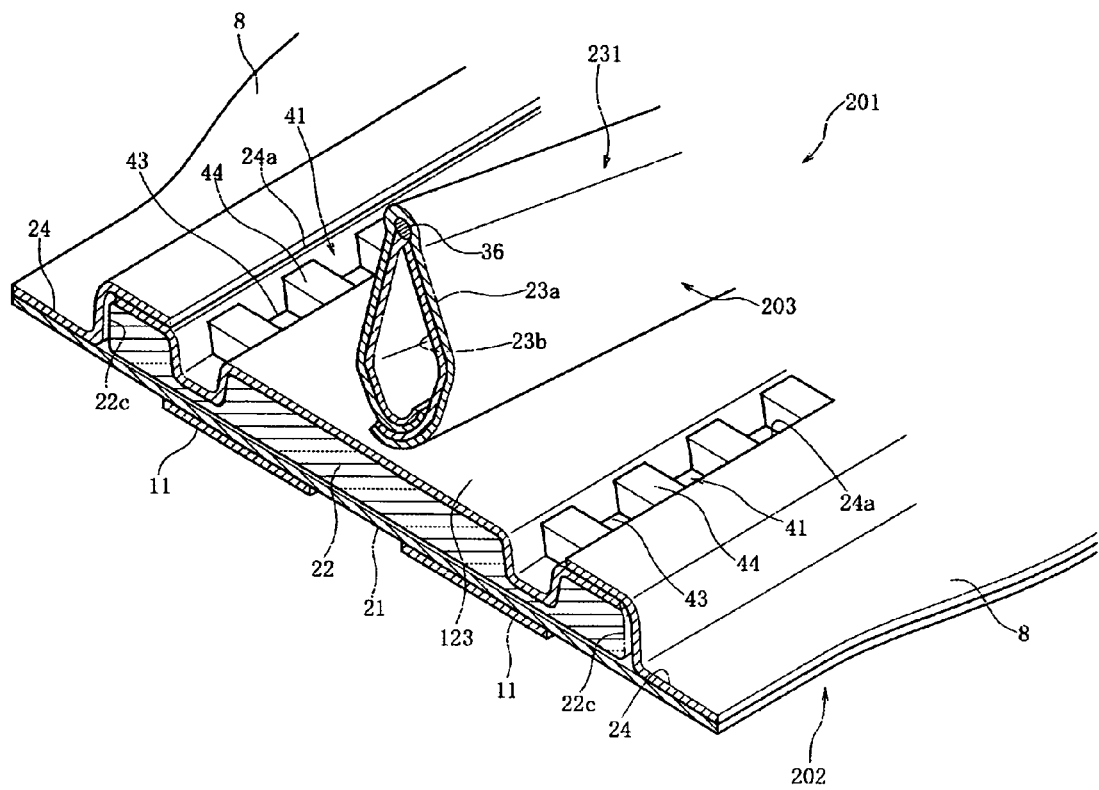
FIG. 9 is a sectional view showing a sanitary napkin according to a third embodiment of the present invention.

FIG. 9 shows a sanitary napkin 201 according to a third embodiment of the present invention and is a sectional view corresponding to FIG. 4.

The sanitary napkin 201 according to the third embodiment has a surface element 203 on a napkin body 202. Between the front and rear ends 34, 35, the surface element 203 provides a protuberance 231 which is separated from the skin-side surface of the napkin body 202 so as to be freely movable in the width direction above the napkin body 202.

The protuberance 231 is formed of the first and second liquid-permeable sheets 23a, 23b and the elastic member 36 is interposed and adhesive-bonded between the first and second liquid-permeable sheets 23a, 23b to extend along the longitudinal centerline Oy. As shown in FIG. 9, the opposite ends of the laminate of the first and second liquid-permeable sheets 23a, 23b are joined together so that the protuberance 231 is of a hollow tubular structure.

In the napkin body 202, the skin-side surface of the liquid absorbent layer 22 is covered with a liquid-permeable topsheet 123. The topsheet 123 is made of the same material as the first and second liquid-permeable sheets 23a, 23b.

Forward of the front end 34 and rearward of the rear end 35, the first and second liquid-permeable sheets 23a, 23b are folded flat to form the front flattened portion 32 and the rear flattened portion 33, respectively. The front and rear flattened portions 32, 33 are adhesive-bonded on the topsheet 123.

When the sanitary napkin 201 according to the third embodiment is used, even if an undergarment is displaced with respect to the wearer's body and the napkin body 202 fixed on an undergarment moves laterally, the protuberance 231 of the sanitary napkin 201 can be kept in the intergluteal cleft 54. Accordingly even if the undergarment is displaced such as by rolling over while sleeping, menstrual blood trying to move posteriorly along the intergluteal cleft can be prevented from leaking out.

Figure 10:
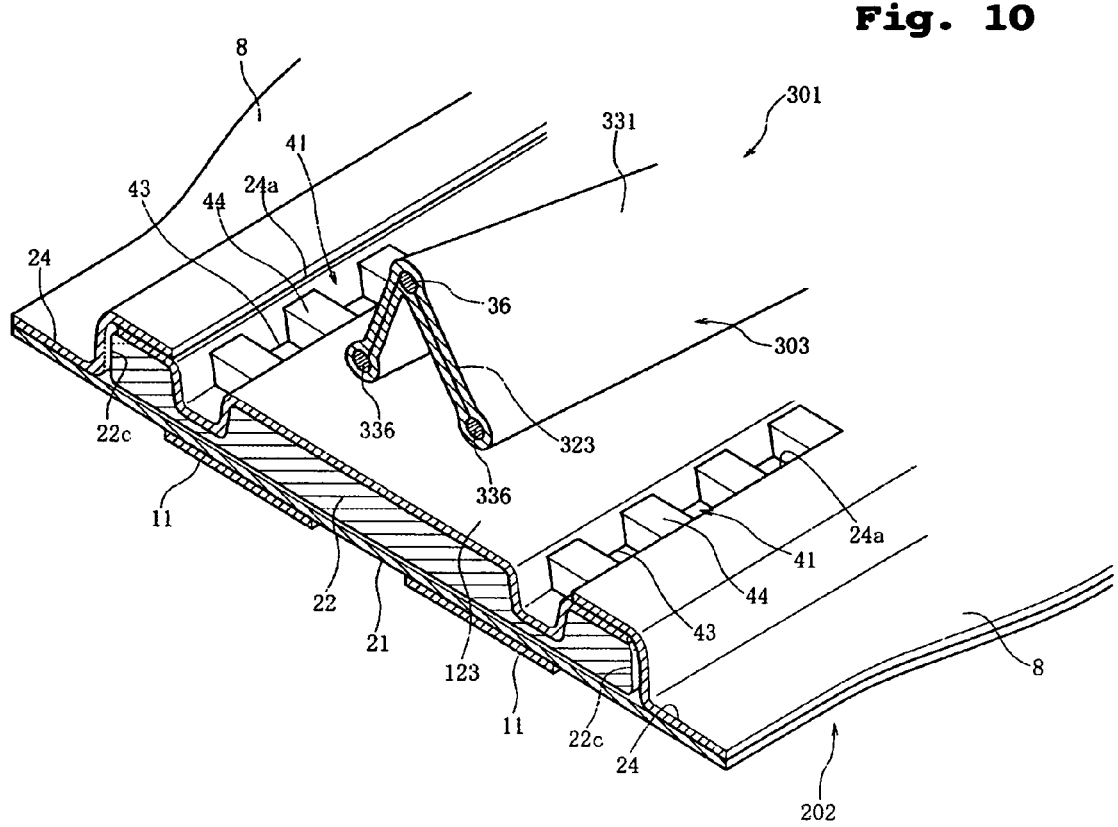
FIG. 10 is a sectional view showing a sanitary napkin according to a fourth embodiment of the present invention.

FIG. 10 shows a sanitary napkin 301 according to a fourth embodiment.

The sanitary napkin 301 has a surface element 303 on the napkin body 202. Between the front and rear ends 34, 35, the surface element 303 also provides a protuberance 331 which is separated from the skin-side surface of the napkin body 202 so as to be freely movable in the width direction above the napkin body 202.

The protuberance 331 is formed by folding a liquid-permeable sheet 323 to have a reversed V-shaped cross-section. Between the folds of the liquid-permeable sheet 323, the elastic member 36 is fixed to extend along the longitudinal centerline Oy. Moreover, additional elastic members 336, 336 are located at equal distances on both sides of the elastic member 36 and also fixed between the folds of the liquid-permeable sheet 323.

This protuberance 331 can provide an improved fit against the intergluteal cleft 54.

FIGS. 11(A), 11(B) and 11(C) are perspective views showing modifications of the protuberance.

FIG. 11(A) shows a protuberance 431A formed of a laminate of three liquid-permeable sheets 423a, 423b, 423c. The protuberance 431A is studded with a plurality of compressed portions 435 where the liquid-permeable sheets 423a, 423b, 423c are locally compressed by embossing.

Menstrual blood having reached the protuberance 431A is concentrated in the compressed portions 435 having a high fiber density and then reaches the liquid absorbent layer 22 along the wall of the protuberance 431A. The protuberance 431A studded with the compressed portions 435 is effective in retaining menstrual blood trying to move posteriorly along the intergluteal cleft 54.

FIG. 11(B) shows a protuberance 431B which has a plurality of elastic members 436 in addition to the elastic member 36 located to extend along the longitudinal centerline Oy. The individual elastic members 436 also exhibit a longitudinal elastic contractive force, but it is preferred that the elastic contractive force of the individual elastic members 436 is weaker than that of the elastic member 36. By making stronger the elastic contractive force of the elastic members 36, the cross-section of the protuberance 31 can be gradually narrowed toward the apex for easy entry into the intergluteal cleft 54, as shown in FIG. 11(B).

FIG. 11(C) shows a protuberance 431C in which a sheet-like elastic member 437 is mounted on an upper portion of a liquid-permeable sheet 423. The elastic member 437 may be a stretch nonwoven fabric with sewn polyurethane yarns, a rubber sheet or a polyurethane sheet. The sheet-like nonwoven fabric 437 is creased to have a reversed V-shaped cross-section and adhesive-bonded to the inner side of the liquid-permeable sheet 423. The sheet-like nonwoven fabric 437 exerts an elastic contractive force to bring the front and rear ends 34, 35 closer to each other, raising the protuberance 431C from the skin-side surface of the napkin body 2.

FIGS. 13 to 17 show various stiffening elements for increasing the stiffness of the rear portion of the napkin body. In the following embodiments, the surface element is identical to that of the first embodiment. However, any one of the foregoing surface elements may be employed.

Figure 13:
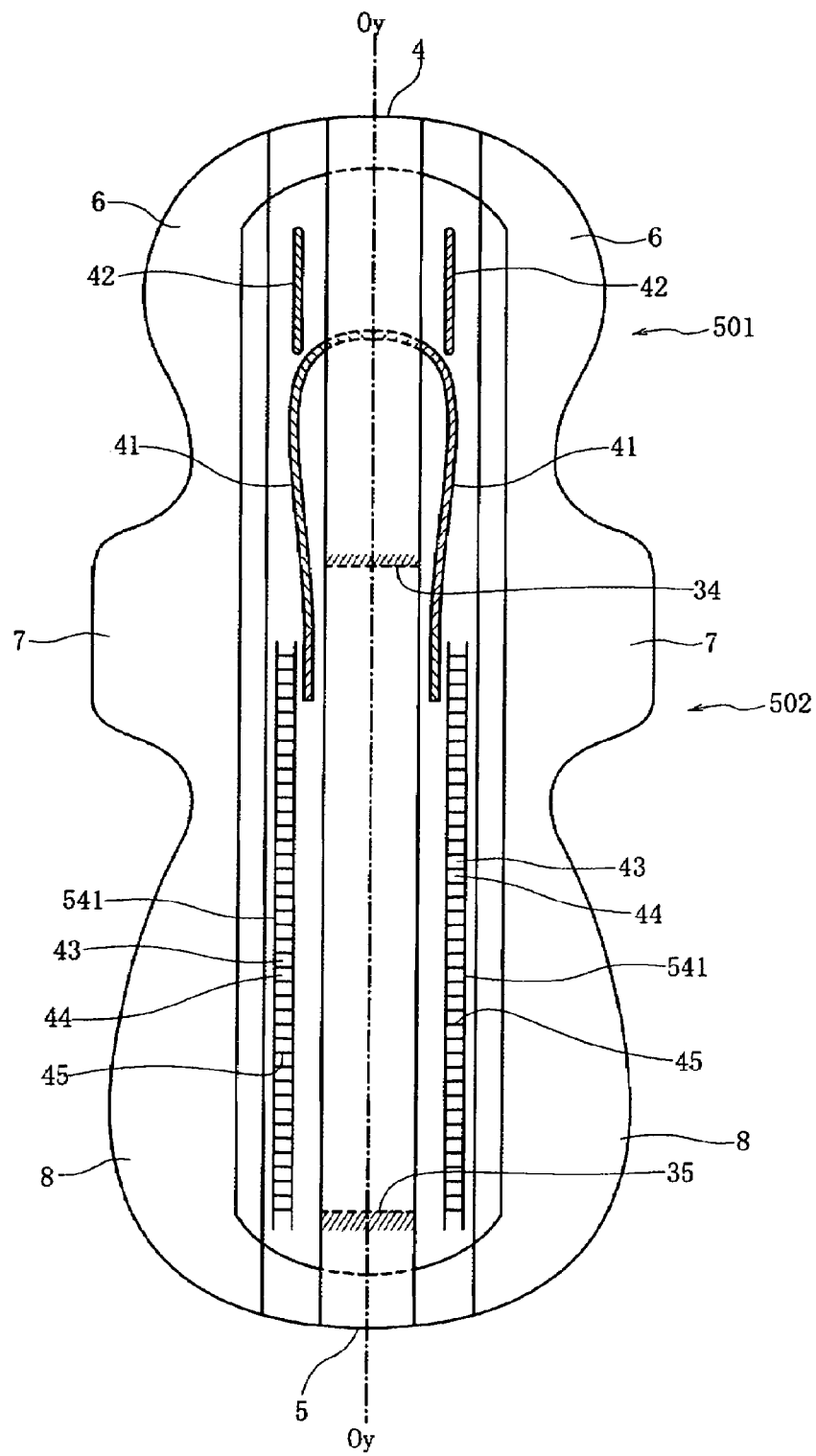
FIG. 13 is a plan view showing a sanitary napkin according to a fifth embodiment of the present invention.

FIG. 13 shows a sanitary napkin 501 according to a fifth embodiment of the present invention and is a plan view corresponding to FIG. 2.

The sanitary napkin 501 has a napkin body 502, of which the front portion has the main compressed line 41 and the front compressed lines 42 like the napkin body 2, but the skin-side surface of the rear portion is formed with rear compressed lines 541, 541 extending parallel to the longitudinal centerline Oy. Preferably, the rear compressed lines 541, 541 are formed in the region where the liquid absorbent layer 22 is present and are not spaced more than 20 mm laterally from the longitudinal centerline Oy. In the present embodiment, rear portions of the main compressed line 41 and the rear compressed lines 541 function as the stiffening element.

The rear compressed lines 541, 541 extend from a position about 5 to 30 mm rearward of the front end 34 to a position rearward of the rear end 35. The rear compressed lines 541, 541 are wider than the main compressed line 41 and formed such that the highly-compressed portions 43 and the weakly-compressed portions 44 alternate with each other in the longitudinal direction, as shown in FIG. 12. It should be noted that all boundary lines 45 between the highly-compressed portions 43 and the weakly-compressed portions 44 of the rear compressed lines 541, 541 are perpendicular to the longitudinal centerline Oy.

Since the boundary lines 45 between the highly-compressed portions 43 and the weakly-compressed portions 44 extend perpendicular to the longitudinal centerline Oy, when an elastic contractive force acts between the front and rear ends 34, 35, the rear portion of the napkin body 502 can be easily curved with the direction of curvature along the longitudinal direction. Moreover, since the wide rear compressed lines 541 are effective in increasing the stiffness, the napkin body 502 can be kept in such a curved state as shown in FIG. 1.

Figure 14:
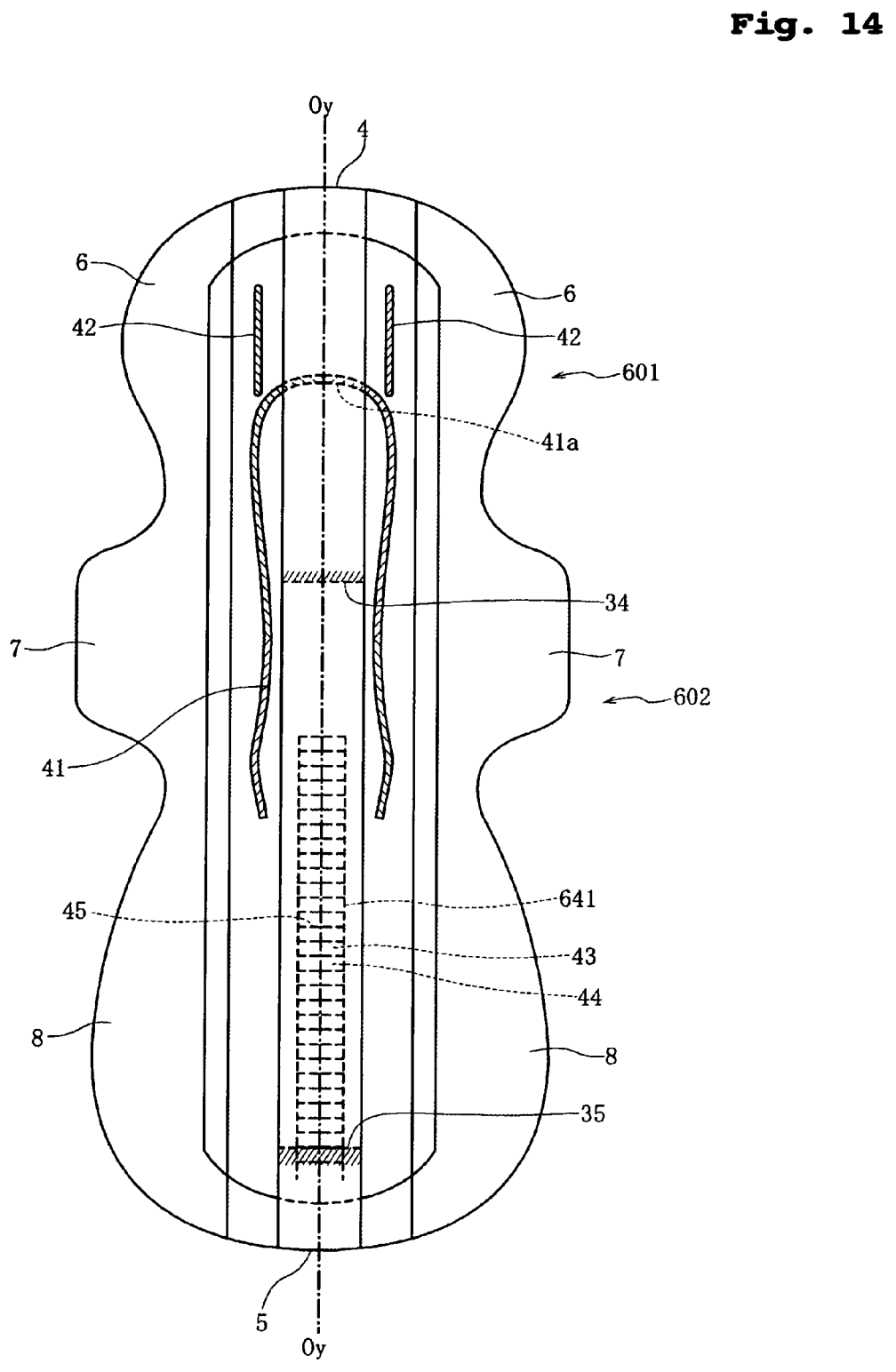

FIG. 14 is a plan view showing a sanitary napkin 601 according to a sixth embodiment of the present invention.

This sixth embodiment is a modification of the fifth embodiment shown in FIG. 13, and the sanitary napkin 601 has a napkin body 602, of which the rear potion is formed with a rear compressed line 641 extending along the longitudinal centerline Oy. In the present embodiment, rear portions of the main compressed line 41 and the rear compressed line 641 function as the stiffening element. In the case where the surface element is identical to that of the first embodiment, the rear compressed line 641 is located beneath the protuberance 31 and between the join boundary lines 37, 37.

The rear compressed line 641, which has a front end spaced rearward from the front end 34, is wider than the main compressed line 41 and formed such that the highly-compressed portions 43 and the weakly-compressed portions 44 alternate with each other in the longitudinal direction. In addition, the boundary lines 45 between the highly-compressed portions 43 and the weakly-compressed portions 44 extend perpendicular to the longitudinal centerline Oy. When an elastic contractive force acts between the front and rear ends 34, 35, therefore, the rear portion of the napkin body 602 can be easily curved with the direction of curvature along the longitudinal direction.

Figure 15:
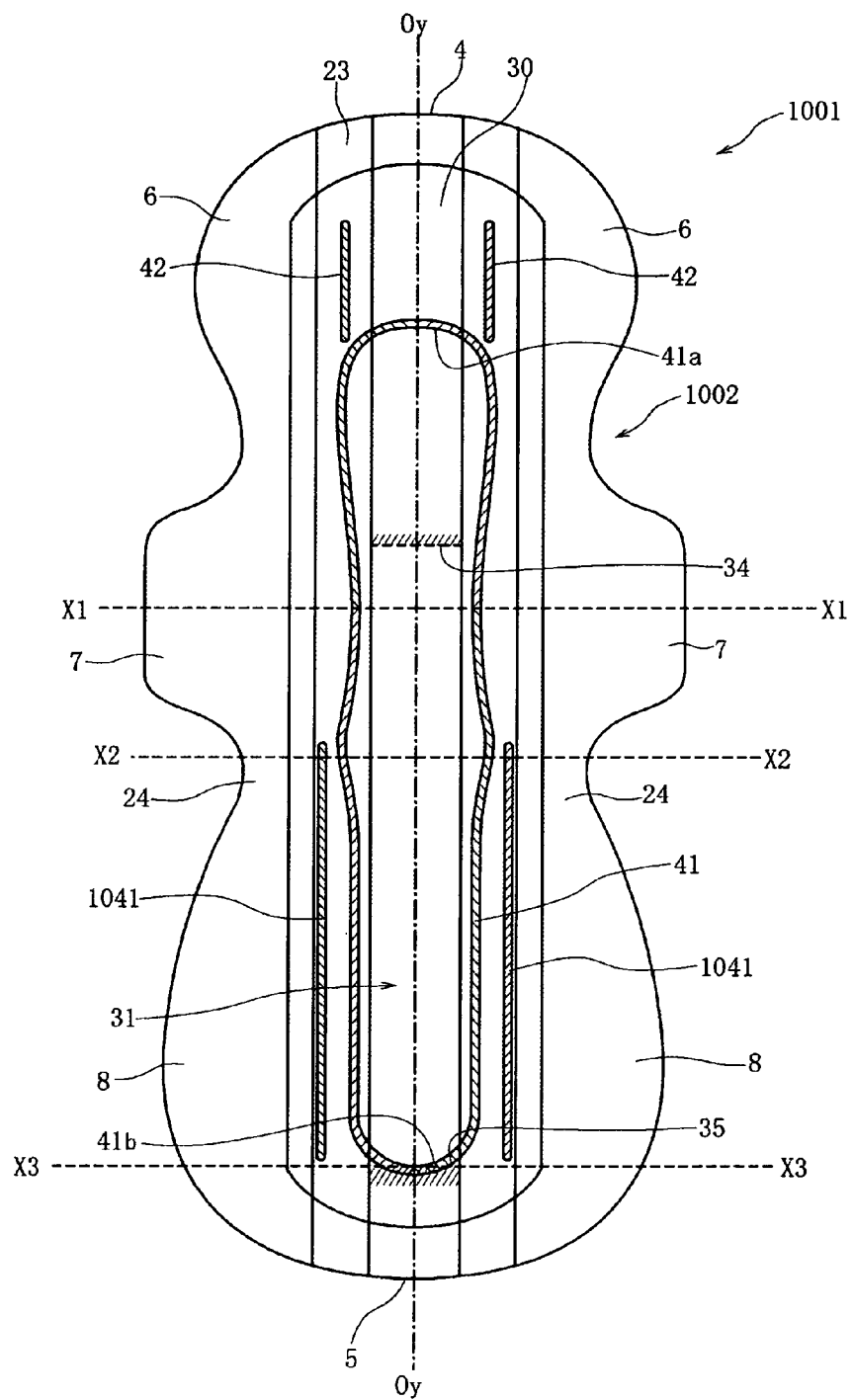
FIG. 15 is a plan view showing a sanitary napkin according to a seventh embodiment of the present invention.

FIG. 15 is a plan view showing a sanitary napkin 1001 according to a seventh embodiment of the present invention.

The sanitary napkin 1001 has a napkin body 1002 that is formed with the main compressed line 41 and the front compressed lines 42, like the napkin body 2 shown in FIGS. 1 and 2. In the intergluteal cleft-facing region from the anus-facing reference line X2 to the coccyx-facing reference line X3, furthermore, rear compressed lines 1041, 1041 are located laterally outside the main compressed line 41. In both the right and left halves of the intergluteal cleft-facing region, therefore, the compressed line is doubled to act as the stiffening element.

Since the compressed line is doubled in both the right and left halves of the intergluteal cleft-facing region, the bending stiffness of the napkin body 1002 can be increased to prevent folding of the napkin body 1002 by the elastic contractive force of the elastic member 36.

It should be noted that in the vagina-facing region between the front end 34 of the protuberance 31 and the anus-facing reference line X2, only the main compressed line 41 functions as the stiffening element. In the present embodiment, accordingly, the compressed line as the stiffening element is not doubled in the right and left halves of the vagina-facing region so that the vagina-facing region can flexibly conform to the shape of the crotch, but doubled in the right and left halves of the intergluteal cleft-facing region so that the napkin body 1002 can be kept in such a curved shape as shown in FIG. 1.

Figure 16:
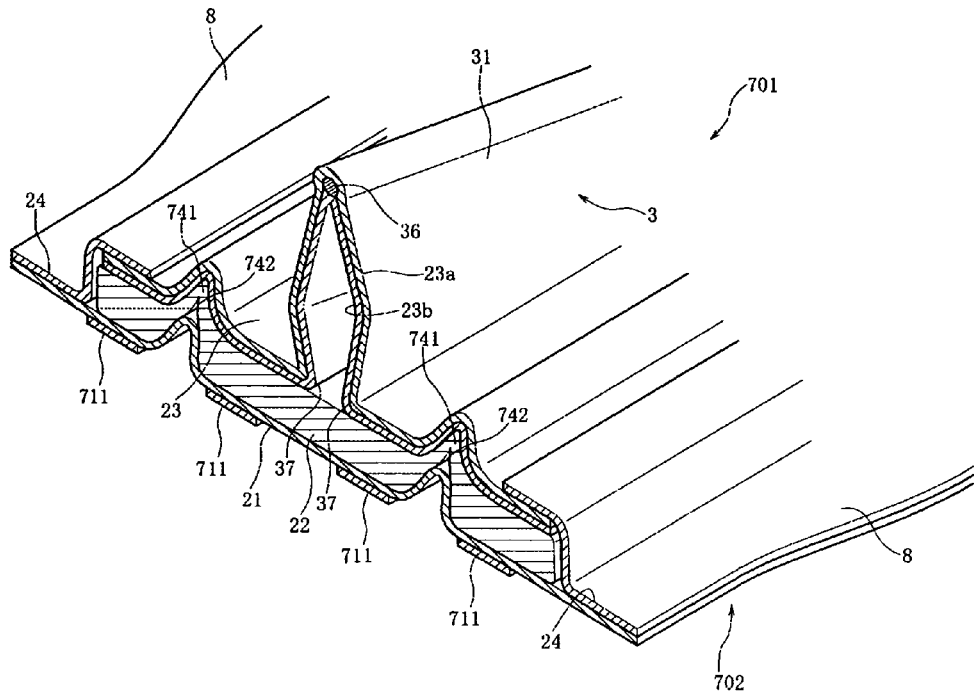
FIG. 16 is a sectional view showing a sanitary napkin according to an eighth embodiment of the present invention.

FIG. 16 is a sectional view showing a sanitary napkin 701 according to an eighth embodiment of the present invention.

The sanitary napkin 701 has a napkin body 702 which provides a stiffening element 741 with the liquid absorbent layer 22 deformed to bulge upward on both sides of the longitudinal centerline Oy. Here, the backsheet 21 is also deformed to bulge upward. At the top of the stiffening element 741, the liquid absorbent layer 22 has a fold line 742. On both sides of the fold line 742, the liquid absorbent layer 22 is compressed in the width direction.

The stiffening element 741 extends from a position forward of the front end 34 to a position rearward of the rear end 35. With the stiffening element 741, the rear portion of the napkin body 702 can be kept in such a curved state as shown in FIG. 1 without being folded.

On the garment-side surface of the napkin body 702, moreover, pressure-sensitive adhesive layers 711 are disposed on both sides of grooves due to formation of the stiffening element 741. When adhered to an undergarment, the pressure-sensitive adhesive layers 711 serve to prevent the bulges of the stiffening element 741 from being flattened out.

Here, the stiffening element 741 may be used in combination with the compressed line. In FIG. 15, for example, the rear compressed lines 1041, 1041 may be replaced by the stiffening element 741.

Figure 17:
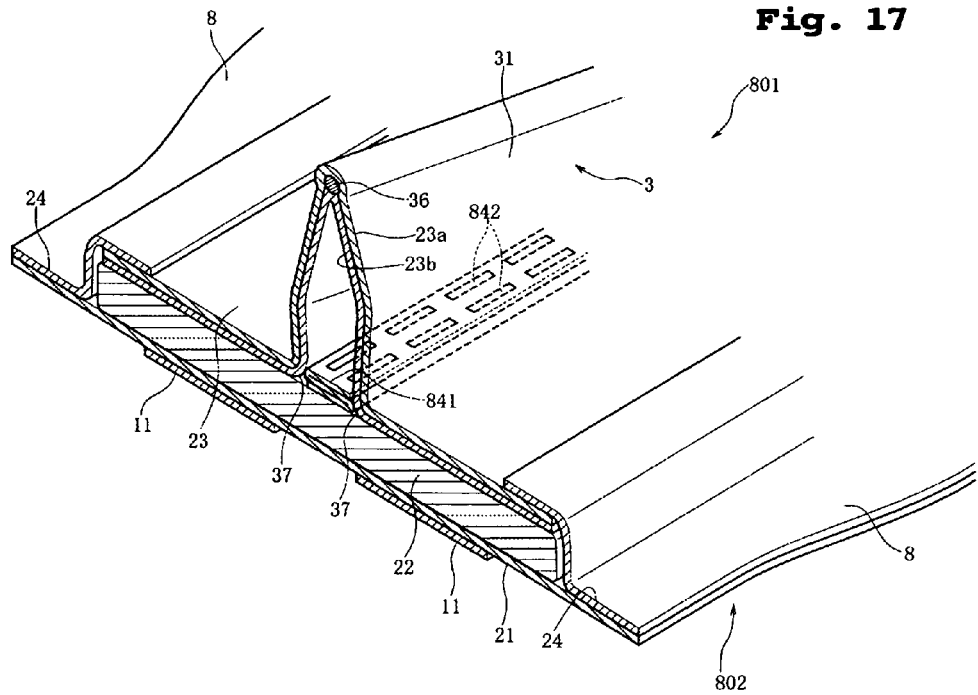
FIG. 17 is a sectional view showing a sanitary napkin according to a ninth embodiment of the present invention.

FIG. 17 shows a sanitary napkin 801 according to a ninth embodiment of the present invention and is a sectional view corresponding to FIG. 4.

The sanitary napkin 801 has a napkin body 802 provided with a reinforcing member 841 as a stiffening element. The reinforcing member 841 is fixed on the skin-side surface of the napkin body 802 between the join boundary lines 37, 37 being the lower ends of the protuberance 31.

As shown in FIG. 17, the reinforcing member 841 is a strip formed by folding a sheet, such as a through-air bonded nonwoven fabric of synthetic resin fibers and an air-laid pulp of which pulp is deposited by an air-laid process and bonded together through a binder. In order to further increase the stiffness, the reinforcing member 841 is embossed to have a number of compressed portions 842. The reinforcing member 841 extends from a position forward of the front end 34 to a position rearward of the rear end 35.

Alternatively, such a strip-shaped reinforcing member may be formed of a resin sheet, a rubber sheet or the like, which is preferably formed with a large number of liquid passage apertures.

Figure 18:
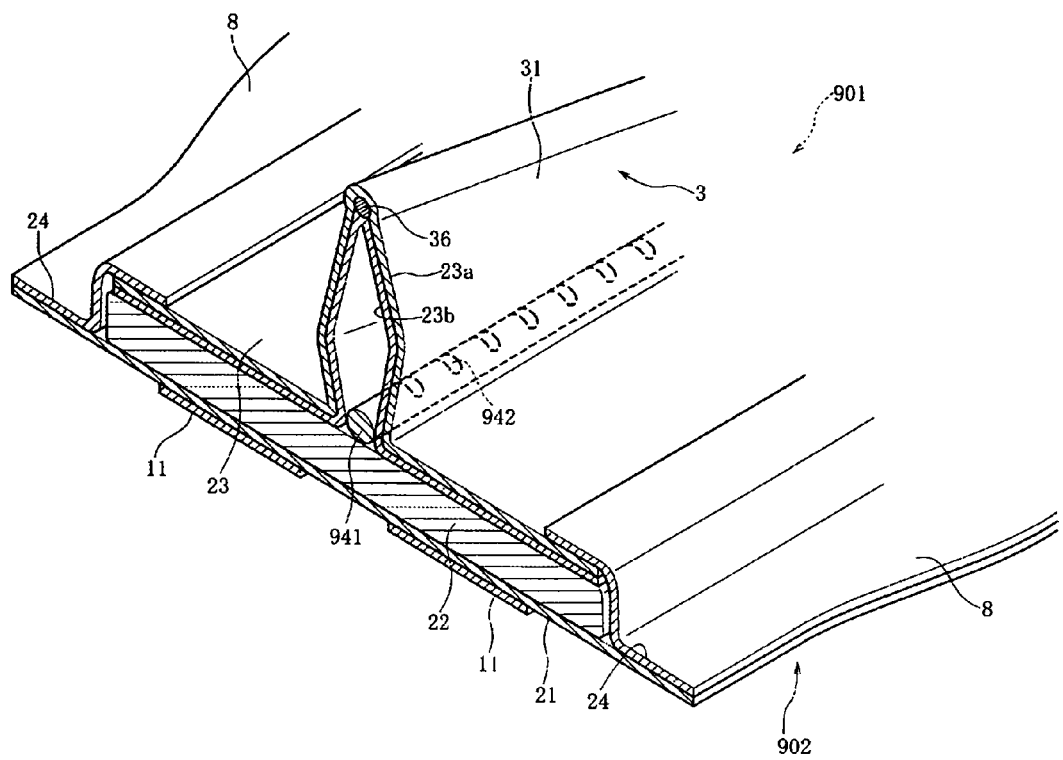
FIG. 18 is a sectional view showing a sanitary napkin according to a tenth embodiment of the present invention.

FIG. 18 is a perspective view showing a sanitary napkin 901 according to a tenth embodiment of the present invention.

The sanitary napkin 901 has a napkin body 902 provided with a reinforcing member 941 as a stiffening element. The reinforcing member 941 may be formed by agglomerating and bonding olefin resin fibers, rayon fibers, pulp or the like into the shape of a rod. Alternatively, it may be formed by rolling an air-laid nonwoven fabric or the like into the shape of a rod or cylinder.

The reinforcing member 941 is bonded to the skin-side surface of the napkin body 902. Recesses 942, which are formed in the upper surface of the reinforcing member 941 at intervals in the longitudinal direction as shown in FIG. 18, facilitate curvature of the rear portion of the napkin body 902 subjected to an elastic contractive force of the elastic member 36.

The stiffening element is not limited to the foregoing embodiments. Between the front and rear ends 34, 35, for example, a hot-melt type adhesive may be applied more on the skin-side surface of the liquid absorbent layer 22 to increase the stiffness.

Although the present invention has been illustrated and described with respect to exemplary embodiments thereof, it should be understood by those skilled in the art that the foregoing and various other changes, omission and additions may be made therein and thereto, without departing from the spirit and scope of the present invention. Therefore, the present invention should not be understood as limited to the specific embodiments set out above but to include all possible embodiments which can be embodied within a scope encompassed and equivalent thereof with respect to the feature set out in the appended claims.

What is claimed is:

1. An elongated sanitary napkin comprising:
a napkin body containing a liquid absorbent layer for absorption and retention of liquid and having a vagina-facing region and an intergluteal cleft-facing region rearward of the vagina-facing region; and
a surface element comprising a front flattened portion, a rear flattened portion, and a protuberance located on a skin-side surface of the napkin body, the protuberance having a front end located in or rearward of the vagina-facing region and a rear end located in or rearward of the intergluteal cleft-facing region and being allowed to rise away from the skin-side surface of the napkin body to have an apex extending in a longitudinal direction of the napkin body between the front and rear ends, the protuberance further rising from the skin-side surface between at least two join boundary lines extending substantially in parallel to the longitudinal direction,
wherein the protuberance is separated from the napkin body at a position between the front and rear ends so as to be freely movable,
wherein the protuberance is hollow and comprises a liquid-permeable nonwoven sheet and an elastic member, the protuberance being positioned substantially over the liquid absorbent layer and the elastic member being configured to exert an elastic contractive force to bring the front and rear ends closer to each other for raising the liquid-permeable sheet away from the skin-side surface of the napkin body,
wherein the protuberance is formed between the front flattened portion and the rear flattened portion, the front and rear flattened portions being formed by folding the liquid-permeable nonwoven sheet, bonding the overlaps and bonding said sheet to the skin-side surface of the liquid absorbent layer,
wherein the sanitary napkin further comprises stiffening elements including compressed portions where the liquid absorbent layer is compressed, the stiffening elements being provided in a rear portion of the napkin body on each side of the protuberance to resist a bending force which acts to bring the front and rear ends closer to each other,
wherein when no external force is exerted on the napkin body, a rising height of the protuberance from the skin-side surface of the napkin body is maximum at a position rearward of the vagina-facing region, and
wherein the compressed portions comprise highly-compressed portions where the skin-side surface of the napkin body is recessed and weakly-compressed portions which have a lower density than the highly-compressed portions and alternate with the highly-compressed portions in the longitudinal direction of the napkin body.

2. The sanitary napkin of claim 1, wherein when the napkin body is mounted on a cylindrical surface having a radius of curvature of 110 mm such that a garment-side surface of the napkin body is in contact with the cylindrical surface with the longitudinal direction of the napkin body being oriented along a direction of curvature of the cylindrical surface and then the protuberance is pushed radially of the cylindrical surface at a position where the rising height is maximum by using a 30 mm diameter circular plane, a force required to depress the protuberance by 5 mm is in the range of 0.05 to 3 N.

3. The sanitary napkin of claim 1, wherein the elastic member is located on or adjacent to a longitudinal centerline of the napkin body so that the apex of the protuberance includes the elastic member.

4. The sanitary napkin of claim 1, wherein a front flattened portion where the liquid-permeable sheet is folded flat is provided forward of the front end with side edges located on both sides of and parallel to a longitudinal centerline of the napkin body.

5. The sanitary napkin of claim 1, wherein the liquid absorbent layer is covered with the liquid-permeable sheet on both sides of the protuberance.

6. The sanitary napkin of claim 1, wherein the stiffening element comprises a main compressed line that extends continuously from a position forward of the front end to a position rearward of the rear end on both sides of said protuberance.

7. An elongated sanitary napkin comprising:
a napkin body containing a liquid absorbent layer for absorption and retention of liquid and having a vagina-facing region and an intergluteal cleft-facing region rearward of the vagina-facing region; and
a surface element comprising a front flattened portion, a rear flattened portion, and a protuberance located on a skin-side surface of the napkin body, the protuberance having a front end located in or rearward of the vagina-facing region and a rear end located in or rearward of the intergluteal cleft-facing region and being allowed to rise away from the skin-side surface of the napkin body to have an apex extending in a longitudinal direction of the napkin body between the front and rear ends, the protuberance further rising from the skin-side surface between at least two join boundary lines extending substantially in parallel to the longitudinal direction, wherein the protuberance is separated from the napkin body at a position between the front and rear ends so as to be freely movable, wherein the protuberance is hollow and comprises a liquid-permeable nonwoven sheet and an elastic member, the protuberance being positioned substantially over the liquid absorbent layer and the elastic member being configured to exert an elastic contractive force to bring the front and rear ends closer to each other for raising the liquid-permeable sheet away from the skin-side surface of the napkin body, wherein the protuberance is formed between the front flattened portion and the rear flattened portion, the front and rear flattened portions being formed by folding the liquid-permeable nonwoven sheet, bonding the overlaps and bonding said sheet to the skin-side surface of the liquid absorbent layer, wherein the sanitary napkin further comprises a stiffening element having a reinforcing member that is incorporated into the napkin body and that underlies the protuberance, said stiffening element including compressed portions where the liquid absorbent layer is compressed and being configured to resist a bending force which acts to bring the front and rear ends closer to each other, wherein when no external force is exerted on the napkin body, a rising height of the protuberance from the skin-side surface of the napkin body is maximum at a position rearward of the vagina-facing region, and wherein the compressed portions comprise highly-compressed portions where the skin-side surface of the napkin body is recessed and weakly-compressed portions which have a lower density than the highly-compressed portions and alternate with the highly-compressed portions in the longitudinal direction of the napkin body.

8. The sanitary napkin of claim 7, wherein the stiffening element comprises a reinforcing member that extends continuously from a position forward of the front end to a position rearward of the rear end.

* * * * *